US008840527B2

(12) United States Patent
Zhang et al.

(10) Patent No.: US 8,840,527 B2
(45) Date of Patent: Sep. 23, 2014

(54) APPARATUS AND METHOD OF CONTROLLING LOWER-LIMB JOINT MOMENTS THROUGH REAL-TIME FEEDBACK TRAINING

(75) Inventors: Li-Qun Zhang, Wilmette, IL (US); Sang Hoon Kang, Chicago, IL (US)

(73) Assignee: Rehabtek LLC, Wilmette, IL (US)

(*) Notice: Subject to any disclaimer, the term of this patent is extended or adjusted under 35 U.S.C. 154(b) by 114 days.

(21) Appl. No.: 13/456,239

(22) Filed: Apr. 26, 2012

(65) Prior Publication Data
US 2012/0277063 A1  Nov. 1, 2012

Related U.S. Application Data

(60) Provisional application No. 61/478,937, filed on Apr. 26, 2011.

(51) Int. Cl.
| *A63B 71/00* | (2006.01) |
| *A61B 5/22* | (2006.01) |
| *A61B 5/00* | (2006.01) |
| *A61B 5/11* | (2006.01) |

(52) U.S. Cl.
CPC ............... *A61B 5/22* (2013.01); *A61B 5/4585* (2013.01); *A61B 5/4595* (2013.01); *A61B 5/112* (2013.01); *A61B 2562/0252* (2013.01)
USPC .......................................................... 482/8

(58) Field of Classification Search
USPC ............... 482/1, 8, 9; 600/300, 587, 592, 595
See application file for complete search history.

(56) References Cited

U.S. PATENT DOCUMENTS

| 4,601,468 | A | * | 7/1986 | Bond et al. ................... 482/7 |
| 4,665,928 | A | * | 5/1987 | Linial et al. ................. 600/595 |
| 4,745,930 | A | * | 5/1988 | Confer ......................... 600/592 |
| 5,476,103 | A | * | 12/1995 | Nahsner ....................... 600/595 |
| 5,551,445 | A | * | 9/1996 | Nashner ....................... 600/595 |
| 5,954,621 | A | * | 9/1999 | Joutras et al. ................ 482/114 |
| 6,162,189 | A | * | 12/2000 | Girone et al. ................ 600/592 |
| 7,278,954 | B2 | * | 10/2007 | Kawai et al. ..................... 482/1 |
| 7,455,620 | B2 | * | 11/2008 | Frykman et al. ................. 482/1 |
| 7,758,470 | B2 | * | 7/2010 | Hirata et al. ...................... 482/7 |
| 7,811,207 | B2 | * | 10/2010 | Stearns et al. .................. 482/52 |
| 7,860,607 | B2 | * | 12/2010 | Kawai et al. ................... 700/245 |
| 8,002,672 | B2 | * | 8/2011 | Brunner ........................... 482/8 |

(Continued)

OTHER PUBLICATIONS

Graves, Sue B. And Juris, Paul M. "A Comparative and Biomechanical Analysis of Two Gait Simulators." Mar. 21, 2007. Florida Atlantic University. <http://media.cybexintl.com/cybexinstitute/research/ArcTrainervsEllipticalStudy.pdf>.*

*Primary Examiner* — Oren Ginsberg
*Assistant Examiner* — Garrett Atkinson

(57) ABSTRACT

An exercise apparatus is disclosed. The exercise apparatus comprises: a three-dimensional coordinate system having an x-axis, a y-axis, and a z-axis; lower limb segments; a moving arm; a multi-axis force sensor; at least one footplate attached to said multi-axis force sensor for supporting a human foot or shoe; a compact real-time ankle motion measurement device, said motion measurement device attached between the leg and foot and capable of measuring the ankle joint motion in at least one degree of freedom; and a central processor, said central processor capable of calculating lower-limb joint moments in real time. The central processor calculates lower-limb joint moments with a modified inverse dynamic method, which does not involve computation of location of center of pressure.

16 Claims, 11 Drawing Sheets

(56) References Cited

U.S. PATENT DOCUMENTS

| | | | |
|---|---|---|---|
| 8,246,555 B2* | 8/2012 | Chiu et al. | 600/595 |
| 8,308,615 B2* | 11/2012 | Vitolo et al. | 482/8 |
| 8,475,339 B2* | 7/2013 | Hwang et al. | 482/8 |
| 8,523,741 B2* | 9/2013 | Chiu et al. | 482/8 |
| 8,571,827 B2* | 10/2013 | Jang et al. | 702/141 |
| 2003/0064869 A1* | 4/2003 | Reinkensmeyer et al. | 482/100 |
| 2004/0097330 A1* | 5/2004 | Edgerton et al. | 482/1 |
| 2004/0167420 A1* | 8/2004 | Song et al. | 600/547 |
| 2004/0219498 A1* | 11/2004 | Davidson | 434/247 |
| 2004/0259690 A1* | 12/2004 | Frykman et al. | 482/8 |
| 2005/0010139 A1* | 1/2005 | Aminian et al. | 600/595 |
| 2005/0033200 A1* | 2/2005 | Soehren et al. | 600/595 |
| 2005/0209536 A1* | 9/2005 | Dariush | 600/595 |
| 2005/0288609 A1* | 12/2005 | Warner et al. | 600/592 |
| 2006/0189899 A1* | 8/2006 | Flaherty et al. | 600/595 |
| 2006/0247095 A1* | 11/2006 | Rummerfield | 482/1 |
| 2006/0282022 A1* | 12/2006 | Dariush | 600/595 |
| 2007/0054777 A1* | 3/2007 | Kawai et al. | 482/1 |
| 2007/0142177 A1* | 6/2007 | Simms et al. | 482/8 |
| 2007/0155588 A1* | 7/2007 | Stark et al. | 482/8 |
| 2009/0082701 A1* | 3/2009 | Zohar et al. | 600/595 |
| 2009/0137366 A1* | 5/2009 | Hirata et al. | 482/9 |
| 2009/0204031 A1* | 8/2009 | McNames et al. | 600/595 |
| 2009/0247370 A1* | 10/2009 | Stearns et al. | 482/52 |
| 2011/0028865 A1* | 2/2011 | Luinge et al. | 600/595 |
| 2011/0208444 A1* | 8/2011 | Solinsky | 702/41 |
| 2011/0218463 A1* | 9/2011 | Hodgins et al. | 600/595 |
| 2012/0021873 A1* | 1/2012 | Brunner | 482/9 |

* cited by examiner

Fig. 7

*$^aM_{F/T\_x}$ and $^aM_{F/T\_y}$ are zero and thus unnecessary, if foot is not strapped to footplate (Winter, 2005).

| Joint | Force/Moment | Kinetic Variable | | | | | | Kinematic Variable | | | |
|---|---|---|---|---|---|---|---|---|---|---|---|
| | | $^aF_{F/T\_x}$ | $^aF_{F/T\_y}$ | $^aF_{F/T\_z}$ | $^aM_{F/T\_x}$* | $^aM_{F/T\_y}$* | $^aM_{F/T\_z}$ | $^o\ddot{y}_a, ^o\ddot{z}_a$ | $^o\ddot{x}_a$ | $\dot{\beta}, \ddot{\beta}$ | $\theta, \dot{\theta}, \ddot{\theta}$ |
| Ankle | $^aF_{ax}$ | X | | | | | | | X | | |
| | $^aF_{ay}$ | | X | | | | | X | | | |
| | $^aF_{az}$ | | | X | | | | X | | | |
| | $^aM_{ax}$ | | X | X | X | | | X | | X | |
| | $^aM_{ay}$ | X | | X | | X | | X | X | X | |
| | $^aM_{az}$ | X | X | | | | X | X | | | |
| Knee | $^kF_{kx}$ | X | | | | | | | X | | $\theta_1, \theta_2, \dot{\theta}_1, \dot{\theta}_2, \ddot{\theta}_1, \ddot{\theta}_2$ |
| | $^kF_{ky}$ | | X | | | | | X | | $\dot{\beta}$ | $\theta_1, \theta_2, \dot{\theta}_1, \dot{\theta}_2, \ddot{\theta}_1, \ddot{\theta}_2$ |
| | $^kF_{kz}$ | | | X | | | | X | | | |
| | $^kM_{kx}$ | | X | X | X* | | X | X | | | $\theta_3, \ddot{\theta}_3$ |
| | $^kM_{ky}$ | X | | X | | X* | X | | X | | $\theta_3, \dot{\theta}_3, \ddot{\theta}_3$ |
| | $^kM_{kz}$ | X | X | | | | X | | | | |

APPARATUS AND METHOD OF CONTROLLING LOWER-LIMB JOINT MOMENTS THROUGH REAL-TIME FEEDBACK TRAINING

BACKGROUND OF INVENTION

More than 21% of adult Americans (46 million) have some form of diagnosed arthritis, and the number is anticipated to rise to 67 million by 2030 (Hootman and Helmick, 2006). The most common type of arthritis, osteoarthritis (OA), affected more than 27 million Americans (Lawrence et al., 2008). Nearly one-half of all adults and two-thirds of those who are obese can now be expected to develop symptomatic knee OA at some point in their lives (Murphy et al., 2008). Knee OA is a major contributor to functional impairment and reduced independence in older adults (Peat et al., 2001).

There is a growing recognition of the role of local neuromechanical factors in influencing physical function and knee OA disease progression. One such factor is varus-valgus laxity and dynamic instability. However, few exercise treatment strategies to target this particular biomechanical and neuromuscular impairment exist.

Although it is well recognized that knee OA is associated with excessive knee adduction moment (KAM) in the frontal plane, there has been a lack of convenient and effective ways of training people with knee OA in better dealing with the frontal plane knee adduction moment loading.

In general, one or more components of lower-limb joint moments may need to be better controlled through feedback training for the purposes of post-injury rehabilitation and injury prevention. There is a general need for real-time feedback training of selected joint moment(s).

The multi-axis rehabilitation system described here addresses such a need and provides us a useful tool to better control a certain joint moment through real-time biofeedback of the targeted joint moment(s).

BRIEF DESCRIPTION OF THE DRAWINGS

FIG. 1 shows schematics of real-time knee moment computation and feedback training

FIG. 7 shows variables needed to be measured on-line for calculation of moments of lower limb joints

COMPONENT LIST

Figure 1A:
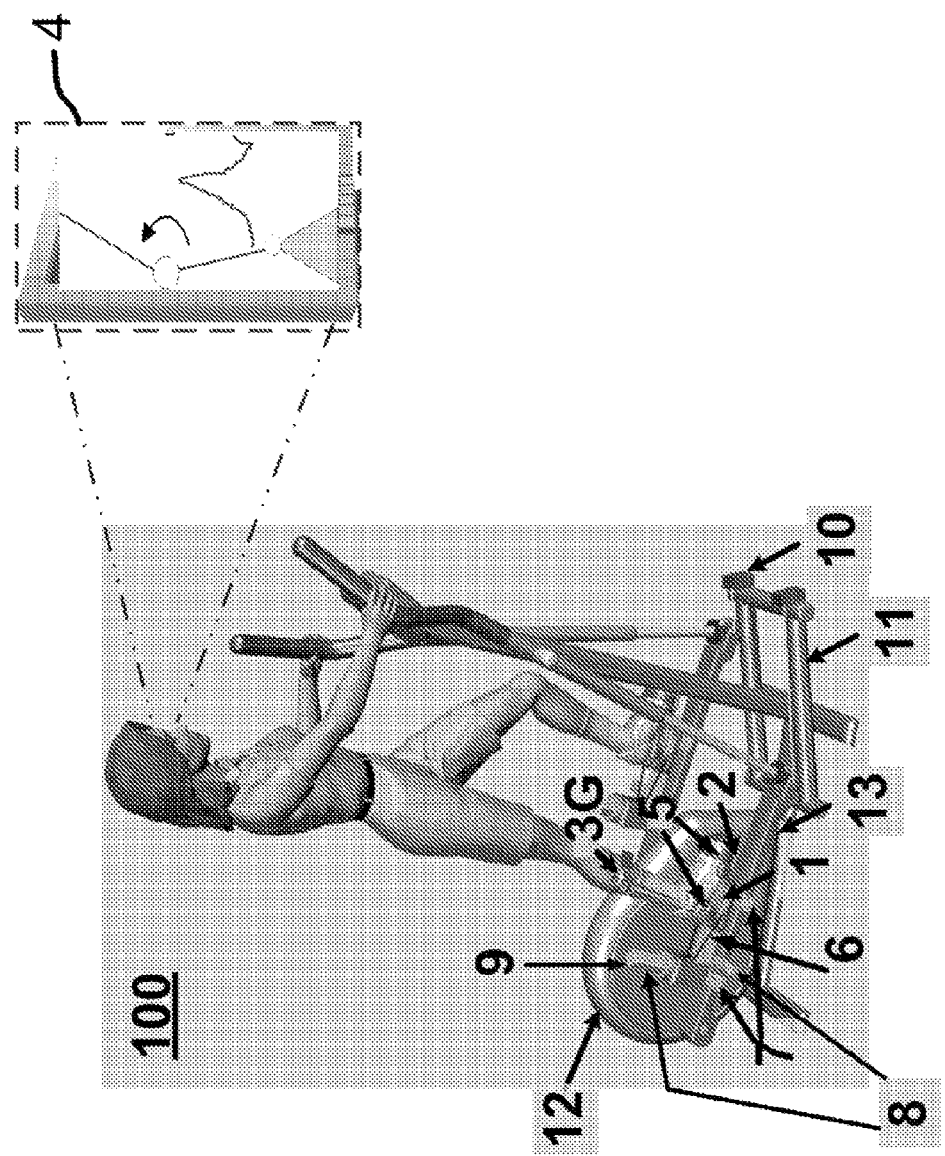
FIG. 1(a) shows a multi-DOF goniometer used as the compact lower-limb motion measurement unit.

1: Multi-axis force sensor
2. Footplate
3G: Multi-DOF goniometer
3I: Inertial measurement unit (IMU)
4: feedback device
5: foot strap
6: pivoting
7: sliding
8: motor
9: position sensor
10: potentiometer
11: oblique ramp
12: driving wheel
13: long beam

DETAILED DESCRIPTION OF THE INVENTION

Figure 1B:
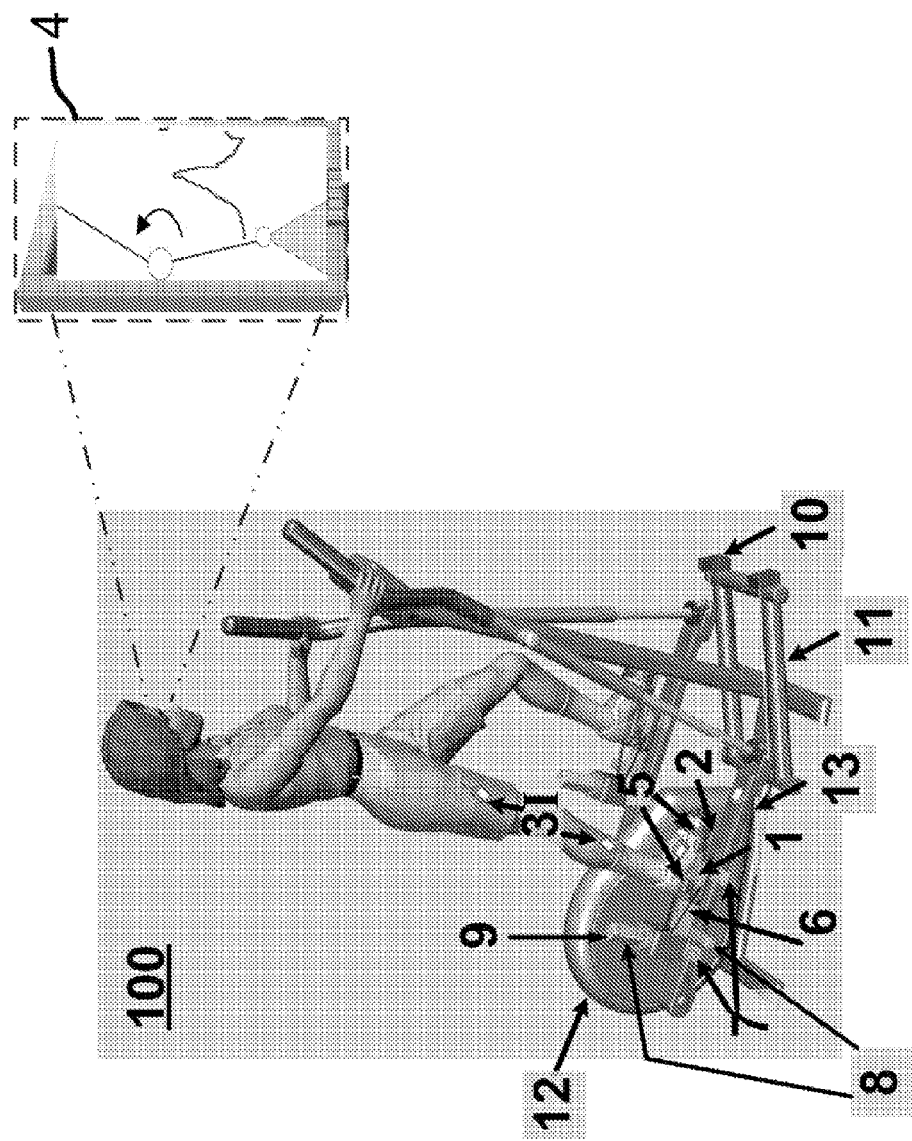
FIG. 1(b) shows an inertial measurement unit used as the compact lower-limb motion measurement unit.

An apparatus and method of 3-dimensional (3-D) knee and ankle moments and forces estimation method are described, which can be used for real-time feedback training on controlling one or more of the 3-D knee and ankle joint moments and forces without requiring the computation of center of pressure (COP)—the location of the vertical ground reaction force (GRF) vector from a force platform (FIG. 1).

The 3-D knee moments under real-time feedback control can be one or more of the moment components including knee flexion-extension, abduction-adduction, and internal-external rotation moments; and the 3-D knee forces can be one or more of the force components including lateral, anterior, and proximal translation forces. The 3-D ankle moments under real-time feedback control can be one or more of the moment components including dorsiflexion-plantar flexion, inversion-eversion and internal-external rotation moments; and the 3-D ankle forces can be one of more force components including lateral, anterior, and proximal translation forces.

For example, knee adduction moment (KAM), a widely used surrogate measure of medial knee compression (Foroughi et al., 2009; Komistek et al., 1999; Miyazaki et al., 2002; Pollo et al., 2002; Reeves and Bowling, 2011; Shelburne et al., 2008; Simic et al., 2011), is significantly correlated with the severity of knee osteoarthritis (OA) (Foroughi et al., 2009; Reeves and Bowling, 2011; Simic et al., 2011), a disease affecting more than 27 million Americans (Lawrence et al., 2008); and is the cause of 60~80% of the compressive load at the medial tibiofemoral knee compartment (Foroughi et al., 2009). Especially, the largest peak of the KAM, which occurs during the load acceptance phase, is the strong predictor of medial compartment OA presence (Simic et al., 2011), radiographic disease severity (Sharma et al., 1998; Simic et al., 2011), rate of progression (Miyazaki et al., 2002), and the presence of OA symptoms (Thorp et al., 2007).

Thus, KAM estimated in real-time may enable the patients with knee OA to use it as a biofeedback in order to control the KAM during locomotion. Considering the wide usage of the ET, the real-time estimation of KAM during ET exercise may be beneficial to millions of patients with knee OA. Until now, there are no reports on real-time biofeedback of the KAM during the training but there are some reports on real-time feedback of dynamic knee frontal alignment (Barrios et al., 2010; Reeves and Bowling, 2011; Simic et al., 2011).

Since the emergence of the biomechanical and gait study, there has been extensive efforts on the estimation of 3D moments (as well as forces) with the advance of measurement technologies (Baker, 2006; Elftman, 1939; Koontz et al., 2006; Shiavi et al., 1987; Whittle, 1996; Winter, 2005; Zhang et al., 2003; Zhou and Hu, 2008), because the 3D moments of lower limb joints are important and provide valuable information in many disciplines including biomechanics, orthopedics, physical rehabilitation, and sports science. Examples are, to name just a few, assessing patients with a walking disorder (Whittle, 1996) based on the normal gait patterns (Elftman, 1939; Riley et al., 2001; Winter, 1984, 1980) and investigating association between KAM and biomechanical variables of patients with knee osteoarthritis (OA) (Foroughi et al., 2009; Hurwitz et al., 2002).

However, most current estimation methods need off-line post processing in order to obtain the moments and forces of lower limb joints. Moreover, there may be other potential difficulties in using readily available methods including a long duration of preparation of attaching markers on the parts of the lower limbs of interest for visual/non-visual motion tracking, occlusion at some points (phases) of gait with visual tracking system (e.g., Optotrak™), drift in the computation of velocity and position from accelerometer data, and distortion of sensed information of magnetic sensors due to the magnetic fields of other devices (e.g., electromagnetic motors and/or ferrite structures) (Zhou and Hu, 2008).

Besides, one of the differences of the proposed robotic multi-axis ET exercise and the ground walking (or the running) is that there is no relative motion between the foot and the footplate, because the bootstrap prevents motion of the foot relative to the footplate. Thus, the foot and the footplate always move together. In other words, the distance between the center of mass (COM) of the foot ($P_{Ft}$) and the center of the 6-axis Force/Torque (F/T) sensor ($P_{F/T}$), which is firmly mounted underneath the footplate, is time-invariant during the exercise. Moreover, due to the movement constraint imposed on the foot and the footplate, non-zero pure moment (also called couple), which is usually ignorable in normal walking and running in a gait lab setting (Cohen et al., 1980), is no longer negligible and may be applied to the footplate. Thus, the typical well established inverse dynamics methods (Winter, 2005; Zatsiorsky, 2002), which require the location of COP, is not applicable to the proposed robotic multi-axis ET exercise. Specifically, with a regular force plate in a gait lab setting, which gives same measured forces/moments as the 6-axis F/T sensor mounted on the proposed robotic multi-axis ET, the COP is computed under the assumption that there is no pure moment exerted on the force plate in the horizontal plane (i.e., zero $T_{ax}$ and $T_{ay}$) (Cohen et al., 1980; Winter, 2005; Zatsiorsky, 2002). Therefore, it might not be applicable to use existing methods developed for the analysis of the over-ground walking and the running, because of the constrained foot movement.

Hence, in order to compute the 3D knee moments as well as other moments including ankle joint moments, a modified inverse dynamic method is described below, which does not involve the computation of location of COP and is tailored for the robotic multi-axis ET exercise.

1. Computation of COP

Figure 3A:
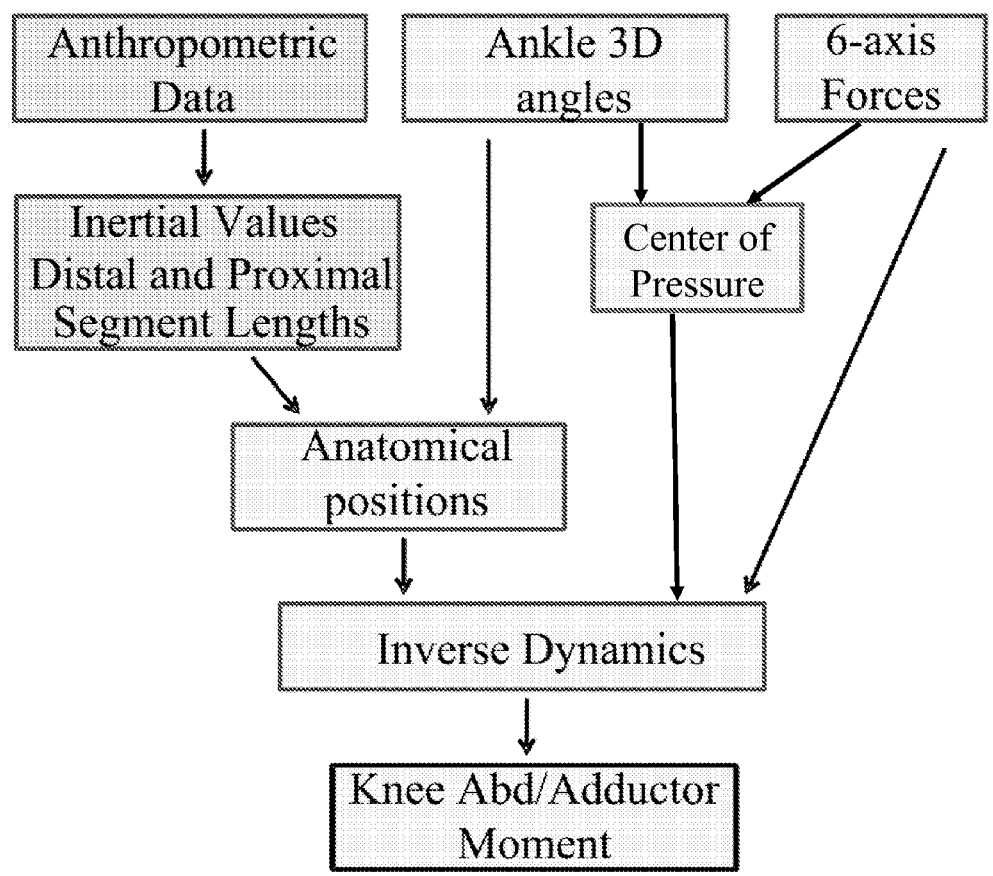
FIG. 3 demonstrates 3D knee moment computation methods, among which 3(a) shows well-known typical methods (Winter, 2005; Zatsiorsky, 2002), and 3(b) shows the proposed method, which does not require COP computation thanks to the features of the proposed robotic multi-axis ET.

For the computation of the 3D knee moments and other lower limb moments, COP is generally needed in order to use well-established inverse dynamics methods based on Newton-Euler equation (Cohen et al., 1980; Winter, 2005; Zatsiorsky, 2002). A typical 3D knee moments computation method (Cohen et al., 1980; Winter, 2005; Zatsiorsky, 2002) may be summarized as follows (FIG. 3($a$)): from the anthropometry data given in (Winter, 2005; Zatsiorsky, 2002) or some other reliable sources, kinematic and dynamic parameters including coordinates of COM, mass and inertia with respect to the COM of each segment (in this case, foot and shank) are obtained; COP is obtained using forces and moments measured with the force plate; translational and rotational accelerations are obtained from a motion tracking device (e.g. Optotrak); one can then compute moment ($M_a \in \Re^3$) and force ($F_a \in \Re^3$) vectors acting on the ankle using the inverse dynamics with GRF and COP; consequently, from $M_a$ and $F_a$ thus computed, knee moment vector ($M_k \in \Re^3$) can be obtained.

Figure 2A:
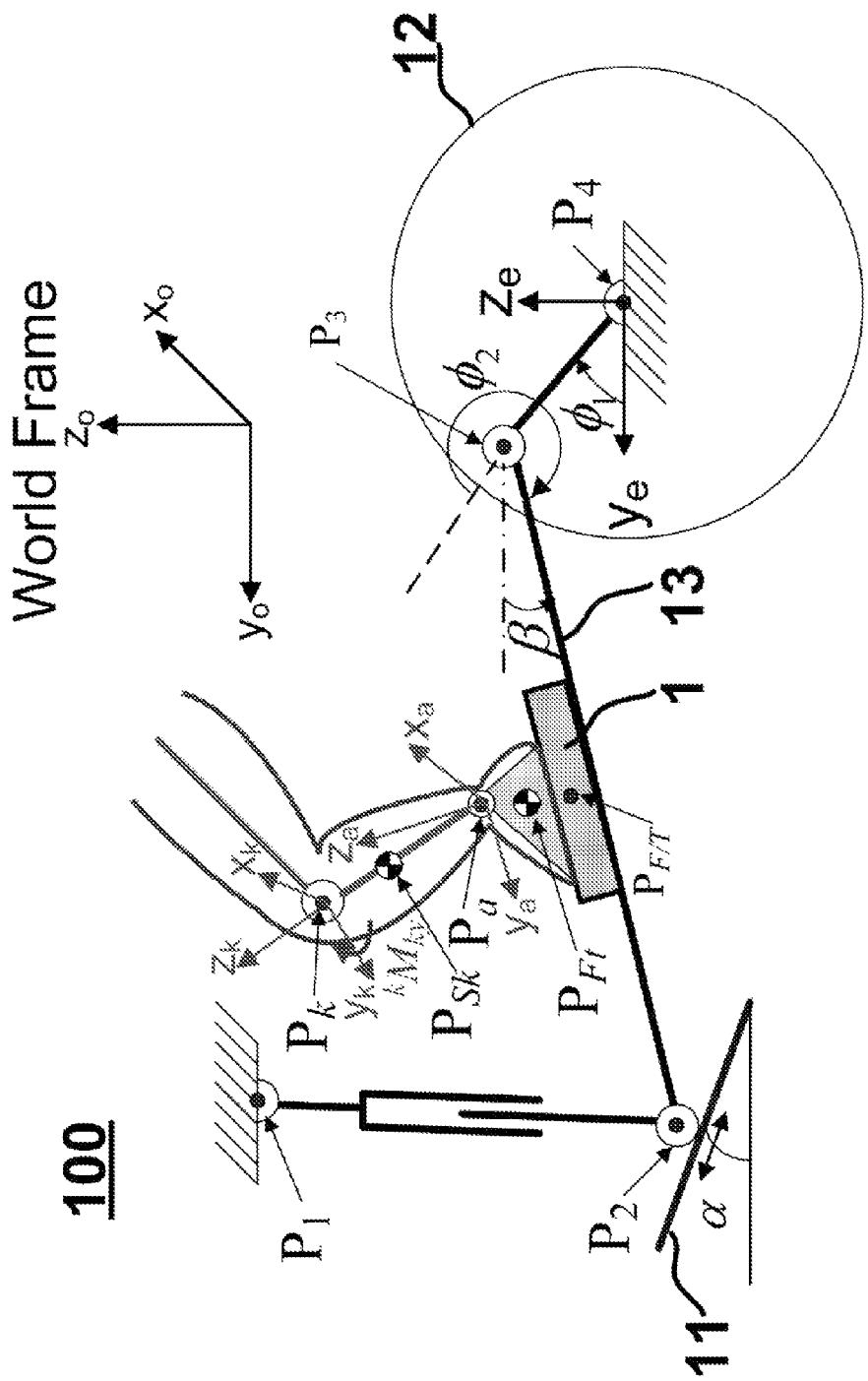
FIG. 2 (a) is a sagittal plane schematic diagram of a right-side lower limb with the proposed robotic multi-axis elliptical trainer (ET).
FIG. 2(b) is a frontal plane free body diagram (FBD) of a foot (triangle), and a 6-axis force/torque (F/T) sensor, located underneath the foot; the top vertex of the triangle, $P_a$, represents ankle JC.
FIG. 2(c) is a FBD of the shank (thick vertical line) with the ankle JC (lower end of the rod) and the knee JC (upper end of the rod).

FIG. 2 ($a$) is the sagittal plane schematic diagram of a right-side lower limb with the proposed robotic multi-axis elliptical trainer (ET). Positive $x_o$ direction is the lateral direction; Positive $y_o$ direction the anterior direction. A circle centered at $P_4$ represents circular disk of the ET. A thick line from $P_2$ to $P_3$ represents the rod where the footplate is mounted on. World frame denotes the frame which is a fixed Lab Ankle frame denotes a frame attached to foot and origin of frame is ankle joint center (JC), $P_a$; knee frame denotes a frame attached to shank and origin of the frame is knee JC, $P_k$. $P_{Sk}$ and $P_{Ft}$ denote positions of center of mass (COM) of the shank and the foot, respectively. FIG. 2($b$) is the frontal plane free body diagram (FBD) of a foot (triangle), and a 6-axis force/torque (F/T) sensor, located underneath the foot; the top vertex of the triangle, $P_a$, represents ankle JC. Positive $y_a$ direction is the anterior direction; positive $x_a$ direction the lateral direction. Since the footplate, which is located between the foot and the 6-axis F/T sensor, is highly stiff, it is omitted for clarity. FIG. 2 ($c$) is FBD of the shank (thick vertical line) with the ankle JC (lower end of the rod) and the knee JC (upper end of the rod). From the forces thus measured with the 6-axis F/T sensor with the 3-dimensional (3D) translational and rotational accelerations of COM of the foot, forces and moments acting on the ankle JC are obtained. Consequently, using forces and moments acting on the ankle JC with the 3D translational and rotational accelerations of COM of the shank, 3D knee moments can be obtained. $d_1$ and $h_1$ denote the $x_a$ and $z_a$ direction coordinate differences between the F/T sensor ($P_{F/T}$), which is the point of action of measured forces/torques, and the COM of the foot (center of white circle, $P_{Ft}$), respectively; $d_2$ and $h_2$ denotes the $x_a$ and $z_a$ direction coordinate differences between the ankle JC($P_a$) and the COM of the foot ($P_{Ft}$), respectively; $^a a_{Ft\_x}$ and $^a a_{Ft\_z}$ the $x_a$ and $z_a$ direction translational accelerations of the COM of the foot, respectively; $^a\ddot{\theta}_{Ft\_y}$, the $y_a$ (frontal) direction rotational acceleration of COM of the foot; $^a F_{F/T\_x}$, $^a F_{F/T\_z}$, $^k F_{F/T\_x}$, and $^k F_{F/T\_z}$ the $x_a$, $z_a$, $x_k$ and $z_k$ direction forces action on the bottom of the foot, respectively; $^a M_{F/T\_y}$ and $^a M_{ay}$ the $y_a$ (frontal) the direction moments measured with the 6-axis F/T sensor and computed at the ankle JC, respectively. $^k M_{ky}$ and $^k M_{ay}$ denote the $y_k$ (frontal) direction moments at the knee JC and the ankle JC, respectively; $^k a_{Sk\_x}$ and $^k a_{Sk\_z}$ the $x_k$ and $z_k$ direction translational accelerations of COM of the shank, respectively; $^a F_{ax}$, $^a F_{az}$, $^k F_{ax}$, and $^k F_{az}$ denote the $x_a$, $z_a$, $x_k$, and $z_k$ direction forces acting on the ankle JC, respectively; $^k F_{kx}$, and $^k F_{kz}$ denote the $x_k$ and $z_k$ direction forces acting on the knee JC, respectively. Specifically, COP is required to compute the net moment acting on the foot. With the measured forces and moments, which correspond to $F_{F/T\_x}$, $F_{F/T\_z}$ and $M_{F/T\_y}$ in FIG. 2, and COP, net resultant foot y direction moment ($M_{y\_net}$), which is equated to the same direction foot inertial torque, can be expressed as follows (Winter, 2005) (Here, for simplicity, it is assumed that the footplate is in horizontal plane (i.e. β=0) and all equations are written with respect to world frame without loss of generality. Thus, left-superscripts, which represent frame of references, are omitted.):

$$M_{y\_net} = F_{F/T\_z}(d_1+x_{cop}) + F_{F/T\_x}h_1 + M_{ay} - F_{az}d_2 + F_{ax}h_2 \qquad (1)$$

where $$h_1 = z_{F/T} - z_{Ft} \qquad (2)$$

$$h_2 = z_a - z_{Ft} \qquad (3)$$

$$d_1 = x_{F/T} - x_{Ft} \qquad (4)$$

$$d_2 = x_a - x_{Ft} \qquad (5)$$

$P_{Ft} = [x_{Ft}\ y_{Ft}\ z_{Ft}]^T$ and $P_a = [x_a\ y_a\ z_a]^T$ denote coordinates of the COM of the foot, and that of ankle, respectively; $x_{cop}$ denotes the x direction coordinate difference between F/T sensor center and the COP, and can be computed as below $$x_{cop} = x_{cp} - x_{F/T} \qquad (6)$$

where $P_{F/T} = [x_{F/T}\ y_{F/T}\ z_{F/T}]^T$ and $P_{cp} = [x_{cp}\ y_{cp}\ z_{cp}]^T$ denote coordinates of center of F/T sensor and that of COP.

Thus, computing location of COP is an important part of the knee moment computation. In (Winter, 2005), of course, a COP computing method with regular force plate when there is no pure moment (also called couple) in horizontal direction (i.e., $x_a$ and $y_a$ direction in FIG. 2(b)) can be found. Again, outputs of regular support force plate are the same as those of the 6-axis F/T sensor mounted on the proposed robotic multi-axis ET.

In general, the y direction moment measured with the 6-axis F/T sensor $M_{F/T\_y}$ can be represented with forces $F_{F/T\_x}$ and $F_{F/T\_y}$ and pure moment $T_y$ as follows (e.g., see AMTI or Bertec technical note or User manual):

$$M_{F/T\_y} = F_{F/T\_x}z_{off} - F_{F/T\_x}x_{cop} + T_y \qquad (7)$$

where $z_{off}$ denotes the z direction distance between center of the 6-axis F/T sensor and the top surface of the sensor (plus footplate thickness). Note that (7) is a generalization of the relation of the COP with the forces and moments acting on a force plate in that, compared with the COP computation method given in Winter (2005), non-zero pure moment $T_y$ is included. It is assumed in (Winter, 2005) that $T_y$ is zero (i.e. $T_y=0$), thus from (7), the x direction component of COP, $x_{cop}$, was obtained as follows:

$$x_{cop} = (F_{F/T\_x}z_{off} - M_{F/T\_y})/F_{F/T\_z} \qquad (8)$$

One disadvantage of using (8) is that if $F_{F/T\_z}$ is small (<2% of body weight), $x_{cop}$ is sensitive to the change of $F_{F/T\_z}$ and thus can be incorrect due to the measurement noise accompanied with $F_{F/T\_z}$ (Winter, 2005). Moreover, if $T_y$ is not zero—which is the case of the proposed robotic multi-axis ET training—COP cannot be computed using (8). It should be noted that the aim of this specific research is not to find COP but to compute 3D knee and ankle moments.

Figure 2B:
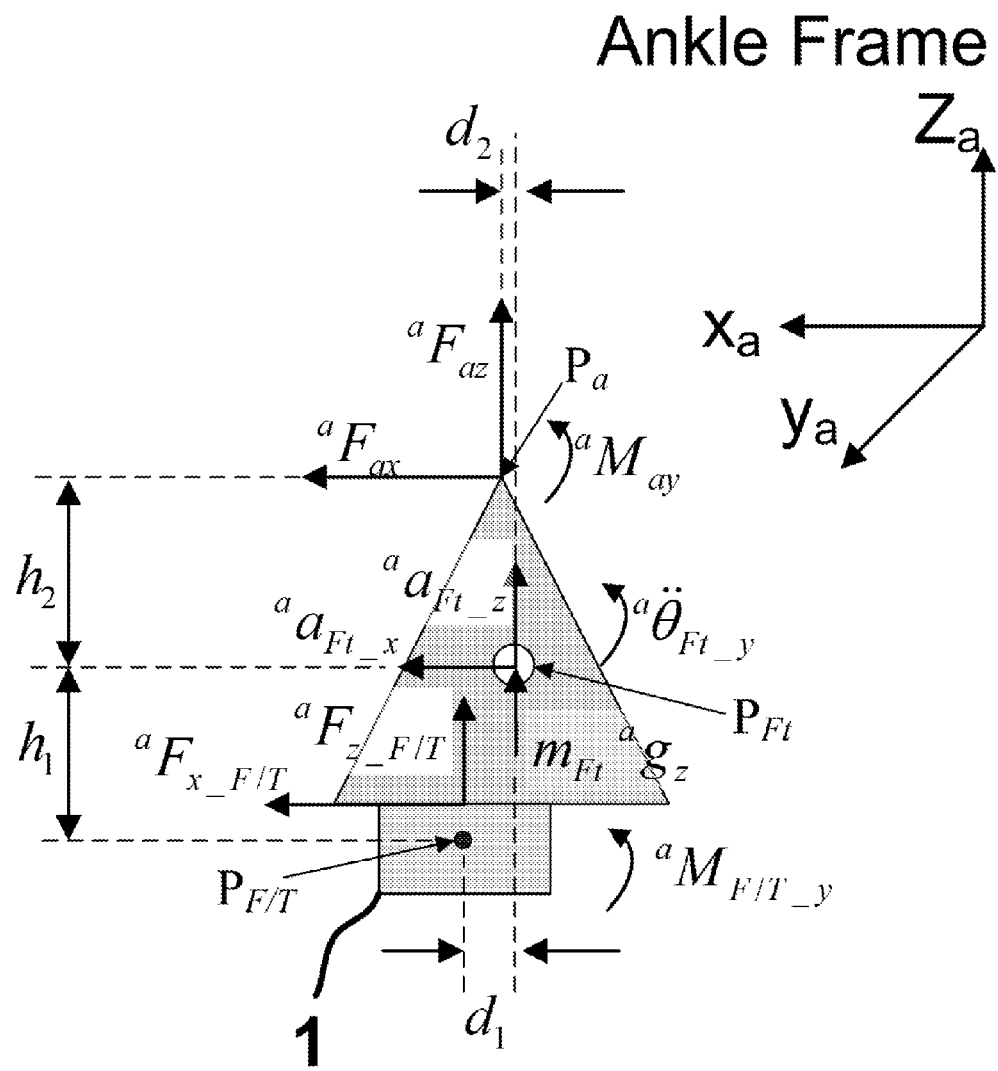

In order to remove the requirement of the COP location from net moment calculation in (1), advantages of the proposed robotic multi-axis ET are utilized. As was mentioned, the distance between the COM of foot ($P_{Ft}$) and the 6-axis F/T sensor ($P_{F/T}$) is fixed; so is the distance between the ankle joint ($P_a$) and the COM of foot ($P_{Ft}$). In other words, once a subject's anthropometric data is obtained, $d_1$, $d_2$, $h_1$ and $h_2$ in FIG. 2(b) are known and time-invariant during the exercise.

Thus, net y direction moment acting on the COM of the foot, $M_{y\_net}$ given in (1), can be rewritten as follows:

$$M_{y\_net} = F_{F/T\_x}h_1 - F_{F/T\_z}d_1 + M_{F/T\_y} + F_{ax}h_2 - F_{az}d_2 + M_{ay} \qquad (9)$$

Obviously, (9) does not require the COP location. Moreover, all the distances ($d_1$, $d_2$, $h_1$ and $h_2$) are time-invariant (i.e., constants) during the exercise. Thus, these distances can be computed off-line, whereas COP requires a real-time online computation for the real-time computation of the 3D knee and ankle moments (and forces). Accordingly, the problem of potential incorrectness of $x_{cop}$ computation in (8) due to high sensitivity under the small $F_{F/T\_z}$ (Winter, 2005) is removed.

Figure 3B:
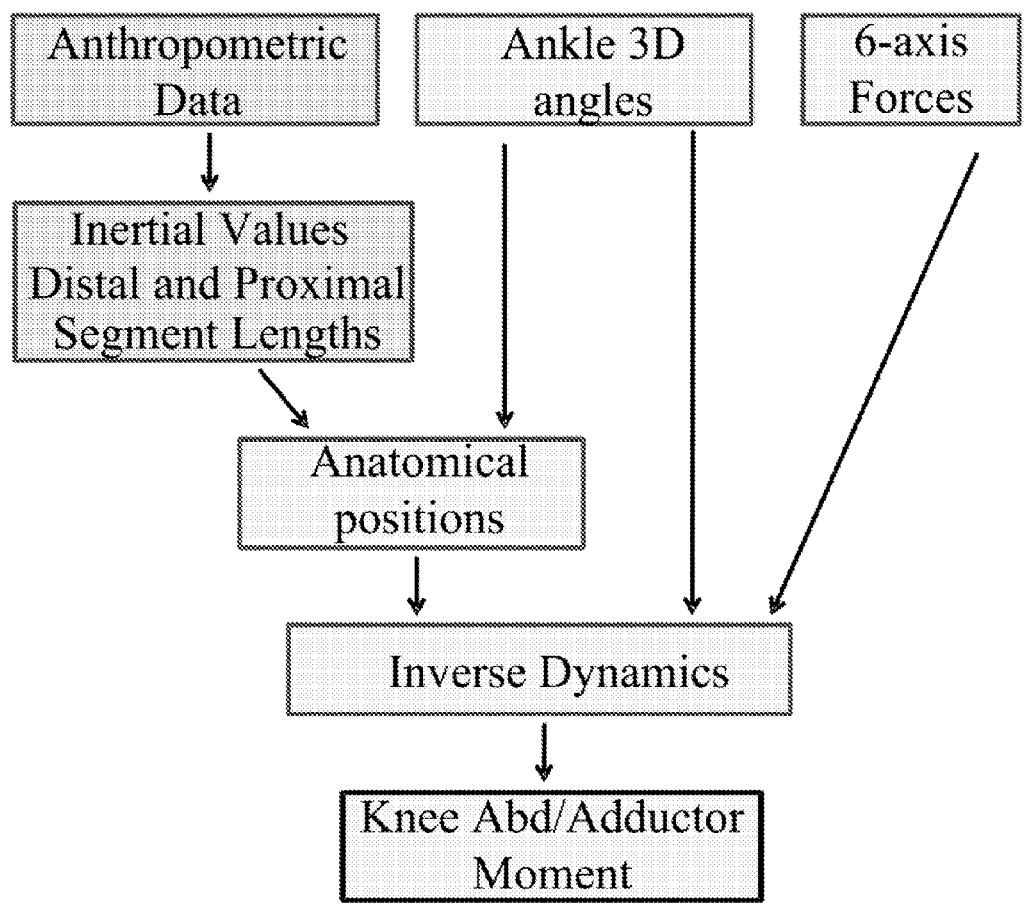

Based on (9), the 3D knee moments and forces (and ankle moments and forces) computation can be simplified as shown in FIG. 3(b). Compared with the typical methods (Cohen et al., 1980; Winter, 2005; Zatsiorsky, 2002), the COP computation is no longer needed.

In short, due to the design of the robotic multi-axis ET, 3D knee and ankle moments and forces can be computed without computing COP location. In the following, the details of the proposed 3D knee and ankle moments computation method are provided by exemplifying the computation of the knee abduction/adduction moment. In case, if the foot is not strapped to footplate, then the usual COP calculation can still be utilized for the computation of knee and ankle forces and moments.

2. Derivation of Dynamic Equations for Real-Time Computation of 3D Moments of Lower Limb Joints In this section, dynamic equations for real-time computation of 3D moments and forces of lower limb joints are provided with a simple 6-DOF goniometer based kinematic measurement technique.

1) Computation of Kinematic Variables

For the computation of 3D knee and ankle moments, kinematic information, which include positions, velocities, and accelerations of the joints and those of COM of segments, and joint angles, angular velocities and accelerations, are required. Specifically, one can compute the 3D knee moments with footplate angle (β), ankle dorsiflexion/planar-flexion ($θ_1$), inversion/eversion ($θ_2$), and shank internal/external rotation ($θ_3$) angles, and shank length ($L_{Sk}$) between knee joint and ankle joint, length between knee joint and COM of shank ($L_{Sk\_com}$), and footplate (or ankle) position, velocity, and acceleration.

A. Kinematic Variables from the Robotic Multi-Axis Elliptical Trainer

Figure 4:
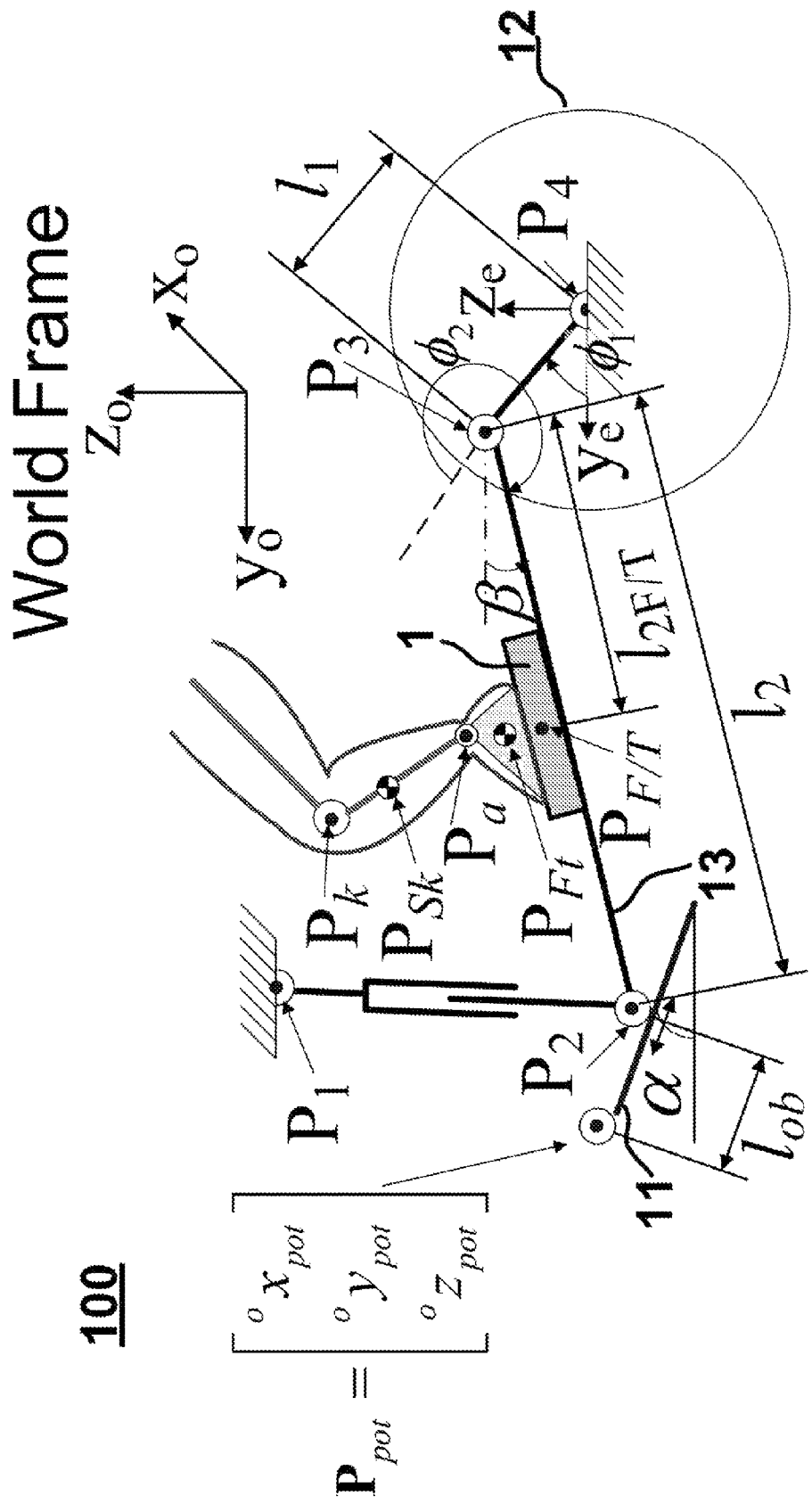
FIG. 4 is a schematic diagram of the robotic multi-axis ET with a lower limb.

FIG. 4 is a schematic diagram of the robotic multi-axis ET with a lower limb. The distance from $P_3$ to $P_4$ is $l_1$; that of road from $P_2$ to $P_3$ is $l_2$; and that of from $P_{F/T}$ to $P_3$ $l_{2FT}$; that of from $P_{pot}$, the location of potentiometer, to $P_2$ $l_{ob}$. $l_1$, $l_2$, and $l_{2FT}$ are known constants in advance once the ET dimension is decide whereas $l_{ob}$ is measured with the potentiometer mounted at fixed point $P_{pot}$. Footplate angle (β) and footplate position can be computed using $P_2$ position (FIG. 4) measured along the oblique ramp direction with a precision potentiometer ($l_{ob}$). Considering the serial linkages from $P_2$ to $P_3$ with length $l_2$ and from $P_3$ to $P_4$ with length $l_1$, because the motion of $P_2$ is constrained by the oblique ramp, once the position of $P_2$ is measured then the two angles ($φ_1$, $φ_2$) can be obtained using a simple inverse kinematics. With the $l_{ob}$ measured and y and z direction coordinates of $P_{pot}$ with respect to the world frame (i.e., $°y_{pot}$ and $°z_{pot}$), one can express they and z coordinates of $P_2$ with respect to the world frame ($°y_2$ and $°z_2$) as follows:

$$\begin{cases} {}^o y_2 = -l_{ob}\cos(\alpha) + {}^o y_{pot} \\ {}^o z_2 = -l_{ob}\sin(\alpha) + {}^o z_{pot} \end{cases} \quad (10)$$

where $\alpha$ denotes the angle between the ground and the oblique ramp in the front part of the robotic multi-axis ET. Since $\alpha$, ${}^o y_{pot}$, and ${}^o z_{pot}$ are constants, once $l_{ob}$ is measured with the potentiometer located at $P_{pot}$, ${}^o y_2$ and ${}^o z_2$ can be obtained.

${}^o y_2$ and ${}^o z_2$ can be also expressed using the two angles ($\phi_1$, $\phi_2$) and lengths ($l_1$ and $l_2$)

$$\begin{cases} {}^o y_2 = l_1\cos(\phi_1) + l_2\cos(\phi_1 + \phi_2) \\ {}^o z_2 = l_1\sin(\phi_1) + l_2\sin(\phi_1 + \phi_2) \end{cases} \quad (11)$$

From (11), $\phi_1$, $\phi_2$ can be obtained as follows (Craig, 1989):

$$\begin{cases} \phi_1 = \tan^{-1}\left(\dfrac{{}^o z_2}{{}^o y_2}\right) - \tan^{-1}\left(\dfrac{l_2\sin(\phi_2)}{l_1 + l_2\cos(\phi_2)}\right) \\ \phi_2 = \tan^{-1}\left(\dfrac{\sin(\phi_2)}{\cos(\phi_2)}\right) \end{cases} \quad (12)$$

where $$\begin{cases} \cos(\phi_2) = \dfrac{{}^o y_2^2 + {}^o z_2^2 - (l_1^2 + l_2^2)}{2l_1 l_2} \\ \sin(\phi_2) = \begin{cases} -\sqrt{1-\cos^2(\phi_2)} & \text{if footplate is in upper position } (180° < \phi_2 \le 360°) \\ \sqrt{1-\cos^2(\phi_2)} & \text{if footplate is in lower position } (0° < \phi_2 \le 180°) \end{cases} \end{cases} \quad (13)$$

Thus, $\phi_1$ and $\phi_2$ can be obtained with ${}^o y_2$ and ${}^o z_2$ directly computed from $l_{ob}$ measured with a potentiometer located at $P_2$. Although there are two inverse kinematics solutions for a given $P_2$ position, however, a correct one can be easily selected with initial condition such as starting position.

With $\phi_1$, $\phi_2$ thus measured, footplate angle ($\beta$) can be easily derived as below $$\beta = \phi_1 + \phi_2 \quad (14)$$

From simple forward kinematics, $P_{F/T}$ the 6-axis F/T sensory and z coordinates with respect to world frame can be computed with $\phi_1$ and $\phi_2$ as below $$\begin{cases} {}^o y_{F/T} = l_1\cos(\phi_1) + l_{2FT}\cos(\phi_1 + \phi_2) \\ {}^o z_{F/T} = l_1\sin(\phi_1) + l_{2FT}\sin(\phi_1 + \phi_2) \end{cases} \quad (15)$$

If the footplate and the 6-axis F/T sensor below the plate is rotating or sliding, angle of rotation or sliding distance can be incorporated into the computation of location of the F/T sensor ($P_{F/T}$) in (15).

B. Kinematic Variables from the 6-DOF Goniometer

Figure 5:
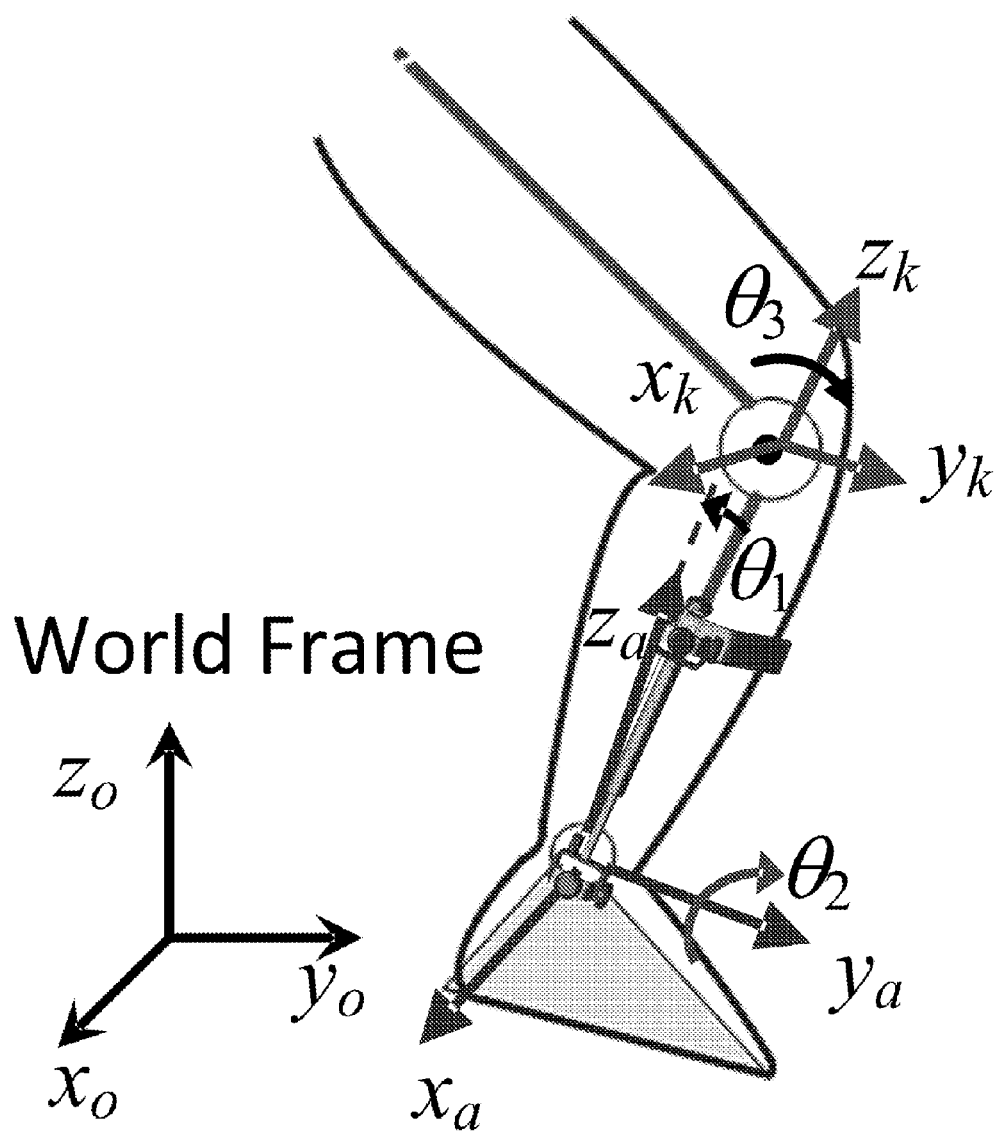
FIG. 5 shows a six-DOF goniometer used to measure ankle dorsiflexion/planar-flexion and inversion/eversion angles and shank internal/external rotation angle accurately in real-time.

FIG. 5 shows a six-DOF goniometer used to measure ankle dorsiflexion/planar-flexion, inversion/eversion, and internal/external rotation angles accurately in real-time. The proximal end is firmly strapped to the bony frontal-medial surface of shank and the distal end is attached to the footplate, which has no motion relative to foot. The ankle joint center (JC), mid-point between the medial and lateral malleoli, was aligned vertically with the F/T sensor center. By using the 6-DOF goniometer, the ankle dorsiflexion/planar flexion angle ($\theta_1$), inversion/eversion angle ($\theta_2$), and internal/external rotation angle ($\theta_3$) can be measured with proper calibration. Rotation angles are defined by following the sequence of x-y-z Euler angle. In order to measure the ankle dorsiflexion/planar-flexion angle ($\theta_1$), inversion/eversion angle ($\theta_2$), and internal/external rotation angle ($\theta_3$) in real-time, a low-cost 6 degree-of-freedom (DOF) goniometer (FIG. 5), which can be conveniently connected to any analog to digital (A/D) data acquisition devices together with other analog signals including the 6-axis forces/torques and locomotion variables, can be utilized without time-consuming preparation (Shiavi et al., 1987; Zhang et al., 2003). The only preparation required is to calibrate the initial angles with a simple calibration plate, on which all potentiometer angles of the 6-DOF goniometer are at known positions (Shiavi et al., 1987; Zhang et al., 2003). Note that the zero angles of 6-DOF goniometer, calibrated with the calibration plate, are not the same as zero anatomical angles of dorsiflexion/planar-flexion, inversion/eversion and internal/external rotation.

In order to calculate the ankle dorsiflexion/planar-flexion, inversion/eversion, and internal/external rotation angle using the 6-DOF goniometer, before start training on ET, subject is asked to stand straight by trying to align knee joint with laser pointer lights coming from lateral (and medial) side and from front. The laser pointer at the lateral side of footplate is aligned with center of F/T sensor (i.e., y coordinate of the laser pointer with respect to ankle frame is the same as that of 6-axis F/T sensor) and can be tilted vertically up and down in $x_a$-$z_a$ plane with respect to ankle frame. The laser pointer at the front size of footplate is located in front of $2^{nd}$ toe (i.e., x coordinate of center of ankle with respect to ankle frame and that of the laser pointer is identical) and also can be tilted vertically up and down in $y_a$-$z_a$ plane with respect to ankle frame. By this way, one can find a posture that can be regarded as 'zero degree posture' (i.e., 0° dorsiflexion/planar-flexion, 0° inversion/eversion, 0° internal/external rotation).

Once the knee joint alignment is confirmed by checking the laser lights, the 6 angles of goniometers and the rotation matrix from the last ($6^{th}$) frame (attached to the bony surface of shank) to the base frame of the 6-axis goniometer (attached to the footplate) at that time (${}_{lg}^{bg}R_i$) are saved. Thus, one can compute rotation matrix from knee frame to ankle frame as follows (Shiavi et al., 1987; Zhang et al., 2003):

$$ {}_k^a R = {}_{lg}^{bg}R ({}_{lg}^{bg}R_i)^{-1} \quad (16)$$

where ${}_{bg}^{lg}R$ denotes rotation matrix from base frame to last frame of the 6-axis goniometer. From ankle dorsiflexion/planar-flexion ($\theta_1$) and inversion/eversion ($\theta_2$) angles and shank internal/external rotation angle ($\theta_3$), ${}_k^a R$ can be also obtained as follows:

$$\begin{aligned}{}_k^a R &= \begin{bmatrix} {}_k^a r_{11} & {}_k^a r_{12} & {}_k^a r_{13} \\ {}_k^a r_{21} & {}_k^a r_{22} & {}_k^a r_{23} \\ {}_k^a r_{31} & {}_k^a r_{32} & {}_k^a r_{33} \end{bmatrix} \\ &= \begin{bmatrix} C\theta_2 C\theta_3 & -C\theta_2 S\theta_3 & S\theta_2 \\ S\theta_1 S\theta_2 C\theta_3 + C\theta_1 S\theta_3 & -S\theta_1 S\theta_2 S\theta_3 + C\theta_1 C\theta_3 & -S\theta_1 C\theta_2 \\ -C\theta_1 S\theta_2 C\theta_3 + S\theta_1 S\theta_3 & C\theta_1 S\theta_2 S\theta_3 + S\theta_1 C\theta_3 & C\theta_1 C\theta_2 \end{bmatrix}\end{aligned} \quad (17)$$

where ${}_k^a r_{ij}$ denotes i,j$^{th}$ element of ${}_k^a R$ obtained from (16). Note that, although the 6-DOF goniometer has a one translational DOF and a potentiometer for measuring the translation, this information is not required for computing $_k^aR$. Clearly, from (16) and (17), one can obtain the three angles ($\theta_1, \theta_2, \theta_3$) as follows:

$$\theta_1 = \tan^{-1}\left(\frac{-_k^a r_{23}}{_k^a r_{33}}\right), \quad (18)$$

$$\theta_2 = \tan^{-1}\left(\frac{_k^a r_{13}}{-S\theta_1 {}_k^a r_{23} + C\theta_1 {}_k^a r_{33}}\right),$$

$$\theta_3 = \tan^{-1}\left(\frac{-_k^a r_{12}}{_k^a r_{11}}\right)$$

From (18), one can select a proper solution because the dorsiflexion/planar-flexion, inversion/eversion and internal/external rotation angles must be between ±90° during normal exercise.

By using a digitizer (e.g., MicroScribe or probe of Optotrak) or referring anthropometric data (Winter, 2005; Zatsiorsky, 2002), the length of shank, $L_{Sk}$, from ankle to knee joint can be measured. Moreover, with $L_{Sk}$ thus measured, the length between knee JC and COM of shank, $L_{Sk\_com}$ can be obtained by referring anthropometric data. Note that the two lengths ($L_{Sk}, L_{Sk\_com}$) are constant values for each subject, thus only one time off-line measurement is required for each subject unless the subject is growing during the training period. Depending on the joint and forces/moments of interest, not all of the angles are required for the computation as shown in FIG. 7.

2) Derivation of Equations of Motion for Computation of 3D Moments of Lower Limb Joints For the derivation of knee moment, available variables, which can be known in advance or measured/estimated, are listed below.

1) Ankle position with respect to the world frame $$^oP_a = [^ox_a {}^oy_a {}^oz_a]^T \quad (19)$$

with respect to the ankle frame $$^aP_a = [0\ 0\ 0]^T \quad (20)$$

and with respect to the knee frame $$^kP_a = [0\ 0\ -L_{Sk}]^T \quad (21)$$

2) Knee position with respect to the knee frame $$^kP_k = [^kx_k {}^ky_k {}^kz_k]^T = [0\ 0\ 0]^T. \quad (22)$$

3) Shank COM position with respect to the knee frame $$^kP_{Sk} = [^kx_{Sk} {}^ky_{Sk} {}^kz_{Sk}]^T = [0\ 0\ -L_{Sk\_com}]^T \quad (23)$$

4) COM of foot position with respect to the ankle frame $$^aP_{Ft} = [^ax_{Ft} {}^ay_{Ft} {}^az_{Ft}]^T \quad (24)$$

which is a constant vector (i.e., $^ax_{Ft}$, $^ay_{Ft}$, and $^az_{Ft}$ are constants).

5) Center of 6-axis F/T sensor position with respect to the ankle frame $$^aP_{F/T} = [^ax_{F/T} {}^ay_{F/T} {}^az_{F/T}]^T \quad (25)$$

which is a constant vector (i.e., $^ax_{F/T}$, $^ay_{F/T}$ and $^az_{F/T}$ are constants).

6) 6-axis measurement of forces and torques exerted on foot by robotic multi-axis ET with respect to the ankle frame $$^aF_{F/T} = [^aF_{F/T\_x} {}^aF_{F/T\_y} {}^aF_{F/T\_z}]^T \quad (26)$$

and $$^aM_{F/T} = [^aM_{F/T\_x} {}^aM_{F/T\_y} {}^aM_{F/T\_z}]^T \quad (27)$$

7) Angular acceleration of foot with respect to the world frame and the ankle frame $$^a\ddot{\theta}_{Ft} = {}^o\ddot{\theta}_{Ft} = [\ddot{\beta}\ 0\ 0]^T. \quad (28)$$

8) Angular velocity and acceleration of shank with respect to the knee frame $$^k\dot{\theta}_{Sk} = \begin{bmatrix} (\dot{\theta}_1 + \dot{\beta})C\theta_2 C\theta_3 + \dot{\theta}_2 S\theta_3 \\ -(\dot{\theta}_1 + \dot{\beta})C\theta_2 S\theta_3 + \dot{\theta}_2 C\theta_3 \\ (\dot{\theta}_1 + \dot{\beta})S\theta_2 + \dot{\theta}_3 \end{bmatrix} \quad (29)$$

$$^k\ddot{\theta}_{Sk} = \begin{bmatrix} (\ddot{\theta}_1 + \ddot{\beta})C\theta_2 C\theta_3 + \ddot{\theta}_2 S\theta_3 - (\dot{\theta}_1 + \dot{\beta})(\dot{\theta}_2 S\theta_2 C\theta_3 + \dot{\theta}_3 C\theta_2 S\theta_3) + \dot{\theta}_2 \dot{\theta}_3 C\theta_3 \\ -(\ddot{\theta}_1 + \ddot{\beta})C\theta_2 S\theta_3 + \ddot{\theta}_2 C\theta_3 + (\dot{\theta}_1 + \dot{\beta})(\dot{\theta}_2 S\theta_2 S\theta_3 - \dot{\theta}_3 C\theta_2 C\theta_3) - \dot{\theta}_2 \dot{\theta}_3 S\theta_3 \\ (\ddot{\theta}_1 + \ddot{\beta})S\theta_2 + \ddot{\theta}_3 + (\dot{\theta}_1 + \dot{\beta})\dot{\theta}_2 C\theta_2 \end{bmatrix} \quad (30)$$

9) Rotation matrix from the ankle frame to the world frame $$^o_aR = \begin{bmatrix} 1 & 0 & 0 \\ 0 & C\beta & -S\beta \\ 0 & S\beta & C\beta \end{bmatrix} \quad (31)$$

10) Rotation matrix from the world frame to the ankle frame $$^a_oR = \begin{bmatrix} 1 & 0 & 0 \\ 0 & C\beta & S\beta \\ 0 & -S\beta & C\beta \end{bmatrix} \quad (32)$$

11) Rotation matrix from the ankle frame to the knee frame $$_a^k R = \begin{bmatrix} C\theta_2 C\theta_3 & S\theta_1 S\theta_2 C\theta_3 + C\theta_1 S\theta_3 & -C\theta_1 S\theta_2 C\theta_3 + S\theta_1 S\theta_3 \\ -C\theta_2 S\theta_3 & -S\theta_1 S\theta_2 S\theta_3 + C\theta_1 C\theta_3 & C\theta_1 S\theta_2 S\theta_3 + S\theta_1 C\theta_3 \\ S\theta_2 & -S\theta_1 C\theta_2 & C\theta_1 C\theta_2 \end{bmatrix} \quad (33)$$

12) Rotation matrix from the knee frame to the world frame $$_k^o R = \begin{bmatrix} C\theta_2 C\theta_3 & -C\theta_2 S\theta_3 & S\theta_2 \\ S(\beta+\theta_1)S\theta_2 C\theta_3 + C(\beta+\theta_1)S\theta_3 & -S(\beta+\theta_1)S\theta_2 S\theta_3 + C(\beta+\theta_1)C\theta_3 & -S(\beta+\theta_1)C\theta_2 \\ -C(\beta+\theta_1)S\theta_2 C\theta_3 + S(\beta+\theta_1)S\theta_3 & C(\beta+\theta_1)S\theta_2 S\theta_3 + S(\beta+\theta_1)C\theta_3 & C(\beta+\theta_1)C\theta_2 \end{bmatrix} \quad (34)$$

13) Gravitational acceleration vector with respect to the world frame $$^o g = [0 \ 0 \ -g]^T \quad (35)$$

with respect to the ankle frame $$^a g = {_o^a R}\, ^o g = [0 \ -gS\beta \ -gC\beta]^T \quad (36)$$

with respect to the knee frame $$^k g = {_a^k R}\, ^a g = \begin{bmatrix} -g[-C(\beta+\theta_1)S\theta_2 C\theta_3 + S(\beta+\theta_1)S\theta_3] \\ -g[C(\beta+\theta_1)S\theta_2 S\theta_3 + S(\beta+\theta_1)C\theta_3] \\ -gC(\beta+\theta_1)C\theta_2 \end{bmatrix}. \quad (37)$$

From (19), (23) and (34), COM of shank position with respect to the world frame can be computed as follows:

$$^o P_{Sk} = \begin{bmatrix} ^o x_a - L_{Sk\_com} S\theta_2 \\ ^o y_a + L_{Sk\_com} S(\theta_1 + \beta) C\theta_2 \\ ^o z_a - L_{Sk\_com} C(\theta_1 + \beta) C\theta_2 \end{bmatrix}. \quad (38)$$

By taking $2^{nd}$ order time derivative of both side (38) and multiplying $_o^k R$, the transpose of $_k^o R$ given in (34), on both side, acceleration of COM of shank, $^k a_{Sk}$, can be obtained as follows:

$$^k a_{Sk} = \begin{bmatrix} C\theta_2 C\theta_3^o \ddot{x}_a + [S(\beta+\theta_1)S\theta_2 C\theta_3 + C(\beta+\theta_1)S\theta_3]^o \ddot{y}_a \\ +[-C(\beta+\theta_1)S\theta_2 C\theta_3 + S(\beta+\theta_1)S - \theta_3]^o \ddot{z}_a \\ +L_{Sk\_com}[C\theta_2 S\theta_3(\ddot{\theta}_1 + \ddot{\beta}) - C\theta_3 \ddot{\theta}_2] \\ +0.5S(2\theta_2)C\theta_3(\dot{\theta}_1 + \dot{\beta})^2 - 2S\theta_2 S\theta_3(\dot{\theta}_1 + \dot{\beta})\dot{\theta}_2] \\ \\ -C\theta_2 S\theta_3{^o \ddot{x}_a} + [C(\beta+\theta_1)C\theta_3 - S(\beta+\theta_1)S\theta_2 S\theta_3]^o \ddot{y}_a \\ +[S(\beta+\theta_1)C\theta_3 + C(\beta+\theta_1)S\theta_2 S\theta_3]^o \ddot{z}_a \\ +L_{Sk\_com}\{+C\theta_2 C\theta_3(\ddot{\theta}_1 + \ddot{\beta}) + S\theta_3 \ddot{\theta}_2\} \\ +0.5S(2\theta_2)S\theta_3(\dot{\theta}_1 + \dot{\beta})^2 - 2\dot{\theta}_2 C\theta_3(\dot{\theta}_1 + \dot{\beta})\dot{\theta}_2\} \\ \\ ^o \ddot{x}_a S\theta_2 - {^o \ddot{y}_a} S(\beta-\theta_1)C\theta_2 + {^o \ddot{z}_a} C(\beta+\theta_1)C\theta_2 \\ +L_{Sk\_com}[\dot{\theta}_2^2 + (\dot{\theta}_1 + \dot{\beta})^2 \ C^2\theta_2] \end{bmatrix} \quad (39)$$

Similarly, from (19), (24), and (31), COM of foot position with respect to the world frame can be obtained as follows:

$$^o P_{Ft} = {^o P_a} + {_a^o R}\, ^a P_{Ft} = \begin{bmatrix} {^a x_{Ft}} + {^o x_a} \\ {^a y_{Ft}} C\beta - {^a z_{Ft}} S\beta + {^o y_a} \\ {^a y_{Ft}} S\beta + {^a z_{Ft}} C\beta + {^o z_a} \end{bmatrix} \quad (40)$$

Thus, from (40), one can get acceleration of COM of foot with respect to the ankle frame.

$$^a a_{Ft} = \begin{bmatrix} {^o \ddot{x}_a} \\ {^o \ddot{y}_a} C\beta + {^o \ddot{z}_a} S\beta - \dot{\beta}^2 \ {^a y_{Ft}} - \ddot{\beta}\, {^a z_{Ft}} \\ -{^o \ddot{y}_a} S\beta + {^o \ddot{z}_a} C\beta + \ddot{\beta}\, {^a y_{Ft}} - \dot{\beta}^2\, {^a z_{Ft}} \end{bmatrix} \quad (41)$$

Because $^a P_{Ft} = [{^a x_{Ft}}\, {^a y_{Ft}}\, {^a z_{Ft}}]^T$ is a constant vector, $^a \dot{x}_{Ft}$, $^a \dot{y}_{Ft}$, $^a \dot{z}_{Ft}$ and $^a \ddot{x}_{Ft}$, $^a \ddot{y}_{Ft}$, $^a \ddot{z}_{Ft}$ are not shown in (41). Note that the aim of this derivation is to compute the knee and ankle moments and forces.

Figure 2C:
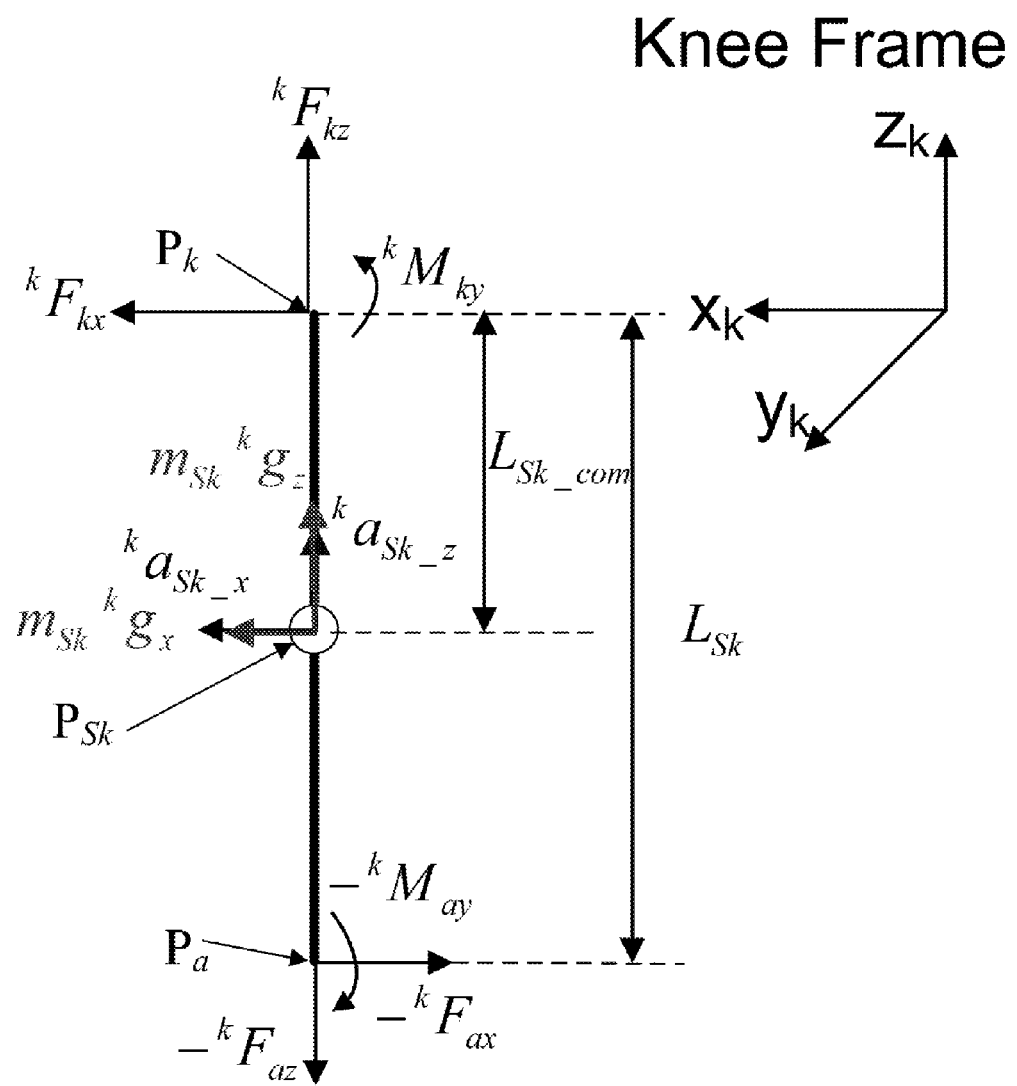

From FIG. 2(c), 6 DOF equation of motion of shank with respect to knee frame can be written as follows:

$$m_{Sk}{^k a_{Sk}} = -{^k F_a} + {^k F_k} + m_{Sk}{^k g} \quad (42)$$

and $$^k I_{Sk}{^k \ddot{\theta}_{Sk}} + {^k \dot{\theta}_{Sk}} \times {^k I_{Sk}}{^k \dot{\theta}_{Sk}} = ({^k P_a} - {^k P_{Sh}}) \times (-{^k F_a}) + ({^k P_k} - {^k P_{Sh}}) \times {^k F_k} - {^k M_a} + {^k M_k} \quad (43)$$

(43) is written with respect to the knee frame, however, in (43), $^k I_{Sk}$ denotes the inertia matrix of shank about its COM, and the moment arms $({^k P_a} - {^k P_{Sh}})$, and $({^k P_k} - {^k P_{Sh}})$ are the vectors from COM of shank to ankle, and to knee, respectively. Thus, (43) can be regarded as the equation of rotational motion of shank with respect to the COM of shank frame—a frame which has the same orientation of the knee frame but its origin is located at COM of shank.

Figure 6:
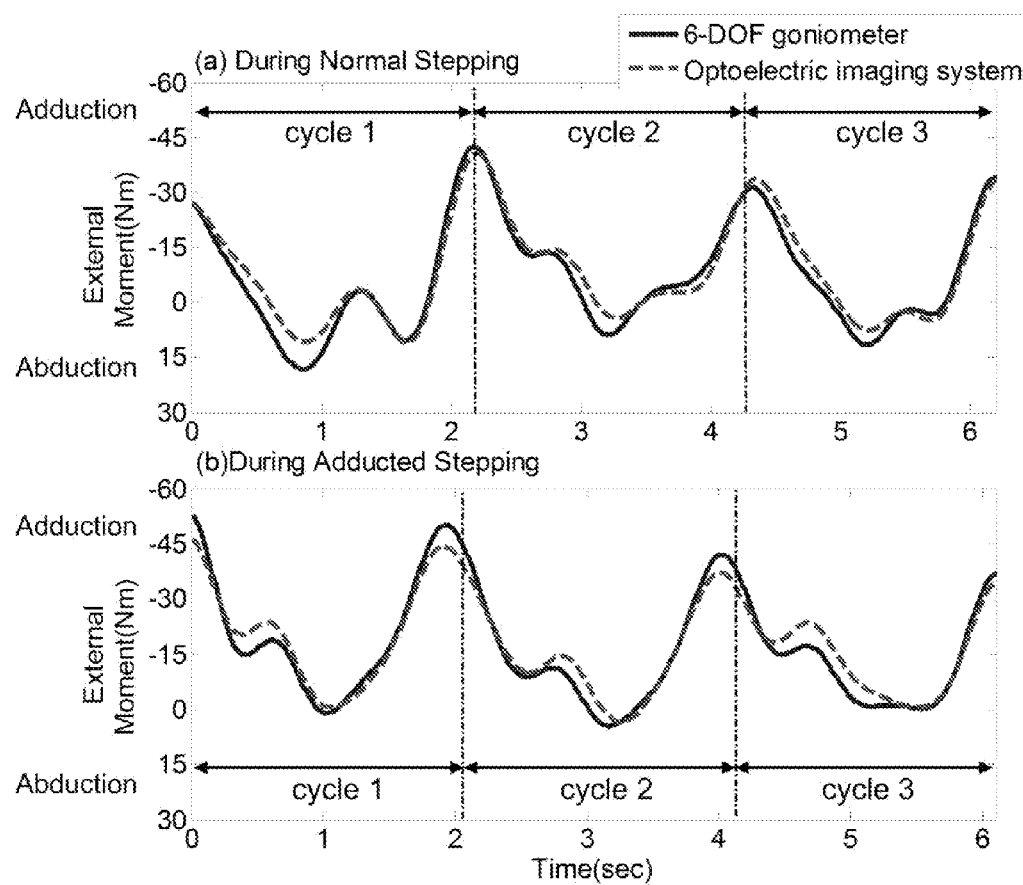
FIG. 6(a) shows knee adduction moment (KAM) estimated during normal stepping.
FIG. 6(b) shows knee adduction moment (KAM) estimated during adducted stepping. In the figures, KAM estimated with the 6-DOF goniometer (blue line) and with the Optotrak (red dashed line) matched each other closely. Peak KAM locations of the two methods in each cycle are almost identical.

Similarly, from FIG. 2(b), 6 DOF equation of motion of foot with respect to the ankle frame can be obtained.

$$m_{Ft}{^a a_{Ft}} = {^a F_{F/T}} + {^a F_a} + m_{Ft}{^a g} \quad (44)$$

$$^a I_{Ft}{^a \ddot{\theta}_{Ft}} = ({^a P_{F/T}} - {^a P_{Ft}}) \times {^a F_{F/T}} + ({^a P_a} - {^a P_{Ft}}) \times {^a F_a} + {^a M_{F/T}} + {^a M_a} \quad (45)$$

Similar to (43), (45) is written with respect to ankle frame, however, in (45), $^a I_{Ft}$ denotes the inertia matrix of foot about its COM, and the moment arms $({^a P_{F/T}} - {^a P_{Ft}})$, and $({^a P_a} - {^a P_{Ft}})$ are the vectors from COM of foot to center of 6-axis F/T sensor, and to ankle, respectively. Thus, (45) can be regarded as the equation of rotational motion with respect to the COM of foot frame—a frame which has the same orientation of ankle frame but its origin is located at COM of foot. Further, because $^a \dot{\theta}_{Ft} = [\dot{\beta}\, 0\, 0]^T$, $^a \dot{\theta}_{Ft} \times {^a I_{Ft}}{^a \dot{\theta}_{Ft}}$ is always a zero vector (we assumed that foot inertia matrix is a diagonal matrix). Thus it is omitted from left-hand-side of (45). Solving (43) for $^k M_k$, we have $$^k M_k = {^k I_{Sk}}{^k \ddot{\theta}_{Sk}} + {^k \dot{\theta}_{Sk}} \times {^k I_{Sk}}{^k \dot{\theta}_{Sk}} - ({^k P_a} - {^k P_{Sh}}) \times (-{^k F_a}) - ({^k P_k} - {^k P_{Sh}}) \times {^k F_k} + {^k M_a} \quad (46)$$

Substituting (20), (22), (23), and (29) into (46) and rearranging it yields $$\begin{bmatrix} {}^kM_{kx} \\ {}^kM_{ky} \\ {}^kM_{kz} \end{bmatrix} = \begin{bmatrix} {}^kI_{Sk\_x}{}^k\ddot{\theta}_{Sk\_x} \\ {}^kI_{Sk\_y}{}^k\ddot{\theta}_{Sk\_y} \\ {}^kI_{Sk\_z}{}^k\ddot{\theta}_{Sk\_z} \end{bmatrix} + \qquad (47)$$

$$\begin{bmatrix} ({}^kI_{Sk\_z} - {}^kI_{Sk\_y})\{(\dot{\theta}_1+\dot{\beta})[-(\dot{\theta}_1+\dot{\beta})S\theta_2C\theta_2S\theta_3 + (\dot{\theta}_2S\theta_2C\theta_3 - \dot{\theta}_3C\theta_2S\theta_3)] + \dot{\theta}_2\dot{\theta}_3C\theta_3\} \\ ({}^kI_{Sk\_x} - {}^kI_{Sk\_z})\{(\dot{\theta}_1+\dot{\beta})[(\dot{\theta}_1+\dot{\beta})S\theta_2C\theta_2C\theta_3 + (\dot{\theta}_2S\theta_2S\theta_3 + \dot{\theta}_3C\theta_2C\theta_3)] + \dot{\theta}_2\dot{\theta}_3S\theta_3\} \\ ({}^kI_{Sk\_y} - {}^kI_{Sk\_x})[(\dot{\theta}_1+\dot{\beta})[-(\dot{\theta}_1+\dot{\beta})C\theta_2S\theta_3C\theta_3 + \dot{\theta}_2C(2\theta_3)]C\theta_2 + \dot{\theta}_2^2S\theta_3C\theta_3] \end{bmatrix} +$$

$$\begin{bmatrix} (L_{Sk} - L_{Sk\_com})^kF_{ay} \\ -(L_{Sk} - L_{Sk\_com})^kF_{ax} \\ 0 \end{bmatrix} + \begin{bmatrix} L_{Sk\_com}{}^kF_{ky} \\ -L_{Sk\_com}{}^kF_{kx} \\ 0 \end{bmatrix} + \begin{bmatrix} {}^kM_{ax} \\ {}^kM_{ay} \\ {}^kM_{az} \end{bmatrix}$$

From (47), one can have the following expression of ${}^kM_k$ $$\begin{cases} {}^kM_{kx} = {}^kI_{Sk\_x}{}^k\ddot{\theta}_{Sk\_x} + {}^kM_{ax} \\ + ({}^kI_{Sk\_z} - {}^kI_{Sk\_y})\{(\dot{\theta}_1+\dot{\beta})[-(\dot{\theta}_1+\dot{\beta})S\theta_2C\theta_2S\theta_3 + (\dot{\theta}_2S\theta_2C\theta_3 - \dot{\theta}_3C\theta_2S\theta_3)] + \dot{\theta}_2\dot{\theta}_3C\theta_3\} \\ + (L_{Sk} - L_{Sk\_com})^kF_{ay} + L_{Sk\_com}{}^kF_{ky} \\ {}^kM_{ky} = {}^kI_{Sk\_y}{}^k\ddot{\theta}_{Sk\_y} + {}^kM_{ay} \\ + ({}^kI_{Sk\_x} - {}^kI_{Sk\_z})\{(\dot{\theta}_1+\dot{\beta})[(\dot{\theta}_1+\dot{\beta})S\theta_2C\theta_2C\theta_3 + (\dot{\theta}_2S\theta_2S\theta_3 + \dot{\theta}_3C\theta_2C\theta_3)] + \dot{\theta}_2\dot{\theta}_3S\theta_3\} \\ - (L_{Sk} - L_{Sk\_com})^kF_{ax} - L_{Sk\_com}{}^kF_{kx} \\ {}^kM_{kz} = {}^kI_{Sk\_z}{}^k\ddot{\theta}_{Sk\_z} + {}^kM_{az} \\ + ({}^kI_{Sk\_y} - {}^kI_{Sk\_x})[(\dot{\theta}_1+\dot{\beta})[-(\dot{\theta}_1+\dot{\beta})C\theta_2S\theta_3C\theta_3 + \dot{\theta}_2C(2\theta_3)]C\theta_2 + \dot{\theta}_2^2S\theta_3C\theta_3] \end{cases} \qquad (48)$$

Substituting (30) into (48) yields ${}^kM_{kx} = {}^kI_{Sk\_x}[(\ddot{\theta}_1+\ddot{\beta})C\theta_2C\theta_3 + \ddot{\theta}_2S\theta_3 - (\dot{\theta}_1+\dot{\beta})(\dot{\theta}_2S\theta_2C\theta_3 + \dot{\theta}_3C\theta_2S\theta_3) + \dot{\theta}_2\dot{\theta}_3S\theta_3]$ $+ ({}^kI_{Sk\_z} - {}^kI_{Sk\_y})\{(\dot{\theta}_1+\dot{\beta})[-(\dot{\theta}_1+\dot{\beta})S\theta_2C\theta_2S\theta_3 + (\dot{\theta}_2S\theta_2C\theta_3 - \dot{\theta}_3C\theta_2S\theta_3)] + \dot{\theta}_2\dot{\theta}_3C\theta_3\}$ $+ (L_{Sk} - L_{Sk\_com})^kF_{ay} + L_{Sk\_com}{}^kF_{ky} + {}^kM_{ax}$ ${}^kM_{ky} = {}^kI_{Sk\_y}[-(\ddot{\theta}_1+\ddot{\beta})C\theta_2S\theta_3 + \ddot{\theta}_2C\theta_3 + (\dot{\theta}_1+\dot{\beta})(\dot{\theta}_2S\theta_2S\theta_3 - \dot{\theta}_3C\theta_2C\theta_3) - \dot{\theta}_2\dot{\theta}_3S\theta_3]$ $+ ({}^kI_{Sk\_x} - {}^kI_{Sk\_z})\{(\dot{\theta}_1+\dot{\beta})[(\dot{\theta}_1+\dot{\beta})S\theta_2C\theta_2C\theta_3 + (\dot{\theta}_2S\theta_2S\theta_3 + \dot{\theta}_3C\theta_2C\theta_3)] + \dot{\theta}_2\dot{\theta}_3S\theta_3\}$ $-(L_{Sk} - L_{Sk\_com})^kF_{ax} - L_{Sk\_com}{}^kF_{kx} + {}^kM_{ay}$ ${}^kM_{kz} = {}^kI_{Sk\_z}[(\ddot{\theta}_1+\ddot{\beta})S\theta_2 + \ddot{\theta}_3 + (\dot{\theta}_1+\dot{\beta})\dot{\theta}_2C\theta_2] + {}^kM_{az}$ $+ ({}^kI_{Sk\_y} - {}^kI_{Sk\_x})[(\dot{\theta}_1+\dot{\beta})[-(\dot{\theta}_1+\dot{\beta})C\theta_2S\theta_3C\theta_3 + \dot{\theta}_2C(2\theta_3)]C\theta_2 + \dot{\theta}_2^2S\theta_3C\theta_3]$ (49)

Substituting (37) into (42) and solving for ${}^kF_k$, we have $${}^kF_k = \begin{bmatrix} m_{Sk}\{{}^ka_{Sk\_x} + g[-C(\beta-\theta_1)S\theta_2C\theta_3 + S(\beta+\theta_1)S\theta_3]\} + {}^kF_{ax} \\ m_{Sk}\{{}^ka_{Sk\_y} + g[C(\beta+\theta_1)S\theta_2S\theta_3 + S(\beta+\theta_1)C\theta_3]\} + {}^kF_{ay} \\ m_{Sk}\{{}^ka_{Sk\_z} + gC(\beta+\theta_1)C\theta_2\} + {}^kF_{az} \end{bmatrix} \qquad (50)$$

Substituting (50) into (49), one can rewrite (49) as follows:

$$\begin{cases} {}^kM_{kx} = {}^kI_{Sk\_x}[(\ddot{\theta}_1+\ddot{\beta})C\theta_2C\theta_3 + \ddot{\theta}_2S\theta_3 - (\dot{\theta}_1+\dot{\beta})(\dot{\theta}_2S\theta_2C\theta_3 + \dot{\theta}_3C\theta_2S\theta_3) + \dot{\theta}_2\dot{\theta}_3S\theta_3] \\ + ({}^kI_{Sk\_z} - {}^kI_{Sk\_y})\{(\dot{\theta}_1+\dot{\beta})[-(\dot{\theta}_1+\dot{\beta})S\theta_2C\theta_2S\theta_3 + (\dot{\theta}_2S\theta_2C\theta_3 - \dot{\theta}_3C\theta_2S\theta_3)] + \dot{\theta}_2\dot{\theta}_3C\theta_3\} \\ + L_{Sk\_com}m_{Sk}\{{}^ka_{Sk\_y} + g[C(\beta+\theta_1)S\theta_2S\theta_3 + S(\beta+\theta_1)C\theta_3]\} + L_{Sk}{}^kF_{ay} + {}^kM_{ax} \\ \\ {}^kM_{ky} = {}^kI_{Sk\_y}[-(\ddot{\theta}_1+\ddot{\beta})C\theta_2S\theta_3 + \ddot{\theta}_2C\theta_3 + (\dot{\theta}_1+\dot{\beta})(\dot{\theta}_2S\theta_2S\theta_3 - \dot{\theta}_3C\theta_2C\theta_3) - \dot{\theta}_2\dot{\theta}_3S\theta_3] \\ + ({}^kI_{Sk\_x} - {}^kI_{Sk\_z})\{(\dot{\theta}_1+\dot{\beta})[(\dot{\theta}_1+\dot{\beta})S\theta_2C\theta_2C\theta_3 + (\dot{\theta}_2S\theta_2S\theta_3 + \dot{\theta}_3C\theta_2C\theta_3)] + \dot{\theta}_2\dot{\theta}_3S\theta_3\} \\ - L_{Sk\_com}m_{Sk}\{{}^ka_{Sk\_x} + g[-C(\beta+\theta_1)S\theta_2C\theta_3 + S(\beta+\theta_1)S\theta_3]\} - L_{Sk}{}^kF_{ax} + {}^kM_{ay} \\ \\ {}^kM_{kz} = {}^kI_{Sk\_z}[(\ddot{\theta}_1+\ddot{\beta})S\theta_2 + \ddot{\theta}_3 + (\dot{\theta}_1+\dot{\beta})\dot{\theta}_2C\theta_2] \\ + ({}^kI_{Sk\_y} - {}^kI_{Sk\_x})[(\dot{\theta}_1+\dot{\beta})[-(\dot{\theta}_1+\dot{\beta})C\theta_2S\theta_3C\theta_3 + \dot{\theta}_2C(2\theta_3)]C\theta_2 + \dot{\theta}_2^2S\theta_3C\theta_3] \\ + {}^kM_{az} \end{cases} \qquad (51)$$

Solving (44) for $^aF_a$ yields $$^aF_a = m_{Ft}{}^a a_{Ft} - {}^aF_{F/T} - m_{Ft}{}^a g \quad (52)$$

Substituting (36) and (41) into (52), we have $$\begin{bmatrix} {}^aF_{ax} \\ {}^aF_{ay} \\ {}^aF_{az} \end{bmatrix} = \begin{bmatrix} m_{Ft}{}^o\ddot{x}_a - {}^aF_{F/T\_x} \\ m_{Ft}({}^o\ddot{y}_a C\beta + {}^o\ddot{z}_a S\beta - \dot{\beta}^2\,{}^ay_{Ft} - \ddot{\beta}{}^az_{Ft}) - {}^aF_{F/T\_y} + m_{Ft}gS\beta \\ m_{Ft}(-{}^o\ddot{y}_a S\beta + {}^o\ddot{z}_a C\beta + \ddot{\beta}{}^ay_{Ft} - \dot{\beta}^2\,{}^az_{Ft}) - {}^aF_{F/T\_z} + m_{Ft}gC\beta \end{bmatrix} \quad (53)$$

Solving (45) for $^aM_a$ yields $$^aM_a = {}^aI_{Ft}{}^a\ddot{\theta}_{Ft} - ({}^aP_{F/T} - {}^aP_{Ft}) \times {}^aF_{F/T} - ({}^aP_a - {}^aP_{Ft}) \times {}^aF_a - {}^aM_{F/T} \quad (54)$$

Substituting (20), (24)-(28), and (53) into (54) and rearranging it yield $$^aM_{ax} = {}^aF_{F/T\_y}{}^az_{F/T} - {}^aF_{F/T\_z}{}^ay_{F/T} - {}^aM_{F/T\_x}$$
$$+ m_{Ft}[-({}^ay_{Ft}S\beta + {}^az_{Ft}C\beta){}^o\ddot{y}_a + ({}^ay_{Ft}C\beta - {}^az_{Ft}S\beta)({}^o\ddot{z}_a + g)]$$
$$+ [{}^aI_{ft\_x} + m_{Ft}({}^ay_{Ft}{}^2 + {}^az_{Ft}{}^2)]\ddot{\beta} \quad (55)$$

$$^aM_{ay} = -{}^aF_{F/T\_x}{}^az_{F/T} + {}^aF_{F/T\_z}{}^ax_{F/T} - {}^aM_{F/T\_y}$$
$$+ m_{Ft}\{{}^az_{Ft}{}^o\ddot{x}_a + {}^ax_{Ft}S\beta{}^o\ddot{y}_a - {}^ax_{Ft}C\beta({}^o\ddot{z}_a + g) - {}^ax_{Ft}{}^ay_{Ft}\ddot{\beta} + {}^ax_{Ft}{}^az_{Ft}\dot{\beta}^2\} \quad (56)$$

and $$^aM_{az} = {}^aF_{F/T\_x}{}^ay_{F/T} - {}^aF_{F/T\_y}{}^ax_{F/T} - {}^aM_{F/T\_z}$$
$$+ m_{Ft}\{{}^ax_{Ft}C\beta{}^o\ddot{y}_a + {}^ax_{Ft}S\beta({}^o\ddot{z}_a + g) - {}^ax_{Ft}{}^az_{Ft}\ddot{\beta} - {}^ax_{Ft}{}^ay_{Ft}\dot{\beta}^2\} \quad (57)$$

By multiplying rotation matrix $^k_aR$, given in (33), on both side of (53) and $^aM_a$, elements of which are given in (55), (56), and (57), one can get $^kF_a$ and $^kM_a$ as follows:

$$^kF_{ax} = -{}^aF_{F/T\_x}C\theta_2 C\theta_3 - {}^aF_{F/T\_y}(S\theta_1 S\theta_2 C\theta_3 + C\theta_1 S\theta_3) + {}^aF_{F/T\_z}(C\theta_1 S\theta_2 C\theta_3 - S\theta_1 S\theta_3)$$
$$+ m_{Ft}\{C\theta_2 C\theta_3{}^o\ddot{x}_a + [S(\beta+\theta_1)S\theta_2 C\theta_3 + C(\beta+\theta_1)S\theta_3]{}^o\ddot{y}_a$$
$$+ [-C(\beta+\theta_1)S\theta_2 C\theta_3 + S(\beta+\theta_1)S\theta_3]({}^o\ddot{z}_a + g)$$
$$+ [-S\theta_2 C\theta_3({}^ay_{Ft}C\theta_1 + {}^az_{Ft}S\theta_1) + ({}^ay_{Ft}S\theta_1 - {}^az_{Ft}C\theta_1)S\theta_3]\ddot{\beta}$$
$$+ [S\theta_2 C\theta_3(-{}^ay_{Ft}S\theta_1 + {}^az_{Ft}C\theta_1) - S\theta_3({}^ay_{Ft}C\theta_1 + {}^az_{Ft}S\theta_1)]\dot{\beta}^2\} \quad (58)$$

$$^kF_{ay} = {}^aF_{F/T\_x}C\theta_2 S\theta_3 + {}^aF_{F/T\_y}(S\theta_1 S\theta_2 S\theta_3 - C\theta_1 C\theta_3) - {}^aF_{F/T\_z}(C\theta_1 S\theta_2 Sf_3 + Sf_1 C\theta_3)$$
$$m_{Ft}\{[-({}^ay_{Ft}C\theta_1 + {}^az_{Ft}S\theta_1)C\theta_3 + ({}^ay_{Ft}S\theta_1 - {}^az_{Ft}C\theta_1)S\theta_2 S\theta_3]\dot{\beta}^2$$
$$+ [({}^az_{Ft}S\theta_1 + {}^ay_{Ft}C\theta_1)S\theta_2 S\theta_3 + ({}^ay_{Ft}S\theta_1 - {}^az_{Ft}C\theta_1)C\theta_3]\ddot{\beta}$$
$$- {}^o\ddot{x}_a C\theta_2 S\theta_3 + [-S(\beta+\theta_1)S\theta_2 S\theta_3 + C(\beta+\theta_1)C\theta_3]{}^o\ddot{y}_a$$
$$+ [C(\beta+\theta_1)S\theta_2 S\theta_3 + S(\beta+\theta_1)C\theta_3]({}^o\ddot{z}_a + g)\} \quad (59)$$

$$^kF_{az} = {}^aF_{F/T\_x}S\theta_2 + {}^aF_{F/T\_y}S\theta_1 C\theta_2 - {}^aF_{F/T\_z}C\theta_1 C\theta_2$$
$$+ m_{Ft}\{+S\theta_2{}^o\ddot{x}_a - S(\beta+\theta_1)C\theta_2{}^o\ddot{y}_a + C(\beta+\theta_1)C\theta_2({}^o\ddot{z}_a + g)$$
$$+ ({}^ay_{Ft}C\theta_1 + {}^az_{Ft}S\theta_1)C\theta_2\ddot{\beta} + ({}^ay_{Ft}S\theta_1 - {}^az_{Ft}C\theta_1)C\theta_2\dot{\beta}^2\} \quad (60)$$

$$^kM_{ax} = ({}^aI_{Ft\_x}\ddot{\beta} - {}^aM_{F/T\_x})C\theta_2 C\theta_3$$
$$- {}^aM_{F/T\_y}(S\theta_1 S\theta_2 C\theta_3 + C\theta_1 S\theta_3) - {}^aM_{F/T\_z}(C\theta_1 S\theta_2 C\theta_3 - S\theta_1 S\theta_3)$$
$$- {}^aF_{F/T\_x}[{}^ay_{F/T}(C\theta_1 S\theta_2 C\theta_3 - S\theta_1 S\theta_3) + {}^az_{F/T}(S\theta_1 S\theta_2 C\theta_3 + C\theta_1 S\theta_3)]$$
$$+ {}^aF_{F/T\_y}[{}^ax_{F/T}(C\theta_1 S\theta_2 C\theta_3 - S\theta_1 S\theta_3) + {}^az_{F/T}C\theta_2 C\theta_3]$$
$$+ {}^aF_{F/T\_z}[{}^ax_{F/T}(S\theta_1 S\theta_2 C\theta_3 + C\theta_1 S\theta_3) - {}^ay_{F/T}C\theta_2 C\theta_3]$$
$$+ m_{Ft}{}^o\ddot{x}_a[{}^ay_{Ft}(C\theta_1 S\theta_2 C\theta_3 - S\theta_1 S\theta_3) + {}^az_{Ft}(S\theta_1 S\theta_2 C\theta_3 + C\theta_1 S\theta_3)]$$
$$+ m_{Ft}{}^o\ddot{y}_a\{{}^ax_{Ft}[-C(\beta+\theta_1)S\theta_2 C\theta_3 + S(\beta+\theta_1)S\theta_3] - ({}^ay_{Ft}S\beta + {}^az_{Ft}C\beta)C\theta_2 C\theta_3\}$$
$$- m_{Ft}({}^o\ddot{z}_a + g)\{{}^ax_{Ft}[S(\beta+\theta_1)S\theta_2 C\theta_3 + C(\beta+\theta_1)S\theta_3] - ({}^ay_{Ft}C\beta - {}^az_{Ft}S\beta)C\theta_2 C\theta_3\}$$
$$- m_{Ft}\ddot{\beta}\{{}^ax_{Ft}[{}^ay_{Ft}(S\theta_1 S\theta_2 C\theta_3 + C\theta_1 S\theta_3) + {}^az_{Ft}(-C\theta_1 S\theta_2 C\theta_3 + S\theta_1 S\theta_3)]$$
$$- ({}^ay_{Ft}{}^2 + {}^az_{Ft}{}^2)C\theta_2 C\theta_3\}$$
$$+ m_{Ft}\dot{\beta}^{2\,a}x_{Ft}[{}^ay_{Ft}(C\theta_1 S\theta_2 C\theta_3 - S\theta_1 S\theta_3) + {}^az_{Ft}(S\theta_1 S\theta_2 C\theta_3 + C\theta_1 S\theta_3)] \quad (61)$$

$$^kM_{ay} = -({}^aI_{Ft\_x}\ddot{\beta} - {}^aM_{F/T\_x})C\theta_2 S\theta_3 - {}^aM_{F/T\_y}(-S\theta_1 S\theta_2 S\theta_3 + C\theta_1 C\theta_3)$$
$$- {}^aM_{F/T\_z}(C\theta_1 S\theta_2 S\theta_3 + S\theta_1 C\theta_3)$$
$$+ {}^aF_{F/T\_x}[{}^ay_{F/T}(C\theta_1 S\theta_2 S\theta_3 + S\theta_1 C\theta_3) - {}^az_{F/T}(-S\theta_1 S\theta_2 S\theta_3 + C\theta_1 C\theta_3)]$$
$$- F_{F/T\_y}[{}^ax_{F/T}(C\theta_1 S\theta_2 S\theta_3 + S\theta_1 C\theta_3) + {}^az_{F/T}C\theta_2 S\theta_3]$$
$$+ {}^aF_{F/T\_z}[{}^ax_{F/T}(-S\theta_1 S\theta_2 S\theta_3 + C\theta_1 C\theta_3) + {}^ay_{F/T}C\theta_1 S\theta_3]$$
$$- m_{Ft}{}^o\ddot{x}_a[{}^ay_{Ft}(C\theta_1 S\theta_2 S\theta_3 + S\theta_1 C\theta_3) - {}^az_{Ft}(-S\theta_1 S\theta_2 S\theta_3 + C\theta_1 C\theta_3)]$$
$$+ m_{Ft}{}^o\ddot{y}_a\{{}^ax_{Ft}[C(\beta+\theta_1)S\theta_2 S\theta_3 + S(\beta+\theta_1)C\theta_3] + ({}^ay_{Ft}S\beta + {}^az_{Ft}C\beta)C\theta_2 S\theta_3\}$$
$$- m_{Ft}({}^o\ddot{z}_a + g)\{{}^ax_{Ft}[-S(\beta+\theta_1)S\theta_2 S\theta_3 + C(\beta+\theta_1)C\theta_3] + ({}^ay_{Ft}C\beta - {}^az_{Ft}S\beta)C\theta_2 S\theta_3\}$$
$$- m_{Ft}\ddot{\beta}\{{}^ax_{Ft}[{}^ay_{Ft}(-S\theta_1 S\theta_2 S\theta_3 + C\theta_1 C\theta_3) + {}^az_{Ft}(C\theta_1 S\theta_2 S\theta_3 + S\theta_1 C\theta_3)]$$
$$+ ({}^ay_{Ft}{}^2 + {}^az_{Ft}{}^2)C\theta_2 S\theta_3\}$$
$$- m_{Ft}\dot{\beta}^{2\,a}x_{Ft}[{}^ay_{Ft}(C\theta_1 S\theta_2 S\theta_3 + S\theta_1 C\theta_3) - {}^az_{Ft}(-S\theta_1 S\theta_2 S\theta_3 + C\theta_1 C\theta_3)] \quad (62)$$

$$^kM_{az} = ({}^aI_{Ft\_x}\ddot{\beta} - {}^aM_{F/T\_x})S\theta_2 + ({}^aM_{F/T\_y}S\theta_1 - {}^aM_{F/T\_z}C\theta_1)C\theta_2$$
$$+ {}^aF_{F/T\_x}({}^ay_{F/T}C\theta_1 + {}^az_{F/T}S\theta_1)C\theta_2 - {}^aF_{F/T\_y}({}^ax_{F/T}C\theta_1 C\theta_2 - {}^az_{F/T}S\theta_2)$$
$$- {}^aF_{F/T\_z}({}^ax_{F/T}S\theta_1 C\theta_2 + {}^ay_{F/T}S\theta_2)$$
$$- m_{Ft}{}^o\ddot{x}_a({}^ay_{Ft}C\theta_1 + {}^az_{Ft}S\theta_1)C\theta_2 - m_{Ft}{}^o\ddot{y}_a[{}^ax_{Ft}C(\beta+\theta_1)C\theta_2 + ({}^ay_{Ft}S\beta + {}^az_{Ft}C\beta)S\theta_2]$$
$$+ m_{Ft}({}^o\ddot{z}_a + g)[{}^ax_{Ft}S(\beta+\theta_1)C\theta_2 + ({}^ay_{Ft}C\beta - {}^az_{Ft}S\beta)S\theta_2]$$

$$+m_{Ft}\ddot{\beta}[(^ay_{Ft}^2+{}^az_{Ft}^2)S\theta_2+{}^ax_{Ft}({}^ay_{Ft}S\theta_1 C\theta_2-{}^az_{Ft}C\theta_1C\theta_2)]$$

$$-m_{Ft}\dot{\beta}^{2a}x_{Ft}({}^ay_{Ft}C\theta_1+{}^az_{Ft}S\theta_1)C\theta_2 \quad (63)$$

Substituting (39), (58), (59) and (60) into (50), one can rewrite (50) as follows:

$$^kF_{kx}=-{}^aF_{F/T\_x}C\theta_2C\theta_3-{}^aF_{F/T\_y}(S\theta_1S\theta_2C\theta_3+C\theta_1S\theta_3)+{}^aF_{F/T\_z}(C\theta_1S\theta_2C\theta_3-S\theta_1S\theta_3)$$

$$+(m_{Sk}+m_{Ft})C\theta_2C\theta_3{}^o\ddot{x}_a+(m_{Sk}+m_{Ft})[S(\beta+\theta_1)S\theta_2C\theta_3+C(\beta+\theta_1)S\theta_3]{}^o\ddot{y}_a$$

$$-(m_{Sk}+m_{Ft})[C(\beta+\theta_1)S\theta_2C\theta_3-S(\beta+\theta_1)S\theta_3]({}^o\ddot{z}_a+g)$$

$$-m_{Ft}\ddot{\beta}[{}^ay_{Ft}(C\theta_1S\theta_2C\theta_3-S\theta_1S\theta_3)+{}^az_{Ft}(S\theta_1S\theta_2C\theta_3+C\theta_1S\theta_3)]$$

$$+m_{Sk}L_{Sk\_com}\{C\theta_2S\theta_3(\ddot{\theta}_1+\ddot{\beta})-C\theta_3S\theta_2-S\theta_2[2S\theta_3(\dot{\theta}_1+\dot{\beta})\dot{\theta}_2+C\theta_2C\theta_3(\dot{\theta}_1+\dot{\beta})^2]\}$$

$$-m_{Ft}\dot{\beta}^2[{}^ay_{Ft}(S\theta_1S\theta_2C\theta_3+C\theta_1S\theta_3)-{}^az_{Ft}(C\theta_1S\theta_2C\theta_3-S\theta_1S\theta_3)] \quad (64)$$

$$^kF_{ky}={}^aF_{F/T\_x}C\theta_2S\theta_3+{}^aF_{F/T\_y}(S\theta_1S\theta_2S\theta_3-C\theta_1C\theta_3)-{}^aF_{F/T\_z}(C\theta_1S\theta_2S\theta_3+S\theta_1C\theta_3)$$

$$-(m_{Sk}+m_{Ft})\{C\theta_2S\theta_3{}^o\ddot{x}_a+[S(\beta+\theta_1)S\theta_2S\theta_3-C(\beta+\theta_1)C\theta_3]{}^o\ddot{y}_a\}$$

$$+(m_{Sk}+m_{Ft})[C(\beta+\theta_1)S\theta_2S\theta_3+S(\beta+\theta_1)C\theta_3]({}^o\ddot{z}_a+g)$$

$$+m_{Ft}\ddot{\beta}[{}^ay_{Ft}(C\theta_1S\theta_2S\theta_3+S\theta_1C\theta_3)+{}^az_{Ft}(S\theta_1S\theta_2S\theta_3-C\theta_1C\theta_3)]$$

$$+m_{Sk}L_{Sk\_com}\{C\theta_2C\theta_3(\ddot{\theta}_1+\ddot{\beta})+S\theta_3S\theta_2+S\theta_2[-2C\theta_3(\dot{\theta}_1+\dot{\beta})\dot{\theta}_2+C\theta_2S\theta_3(\dot{\theta}_1+\dot{\beta})^2]\}$$

$$+m_{Ft}\dot{\beta}^2[{}^ay_{Ft}(S\theta_1S\theta_2S\theta_3-C\theta_1C\theta_3)-{}^az_{Ft}(C\theta_1S\theta_2S\theta_3+S\theta_1C\theta_3)] \quad (65)$$

$$^kF_{kz}=-{}^aF_{F/T\_x}S\theta_2+{}^aF_{F/T\_y}S\theta_1C\theta_2-{}^aF_{F/T\_z}C\theta_1C\theta_2$$

$$+(m_{Sk}+m_{Ft})[S\theta_2{}^o\ddot{x}_a-S(\beta+\theta_1)C\theta_2{}^o\ddot{y}_a]+(m_{Sk}+m_{Ft})C(\beta+\theta_1)C\theta_2({}^o\ddot{z}_a+g)$$

$$+m_{Ft}\ddot{\beta}({}^az_{Ft}S\theta_1+{}^ay_{Ft}C\theta_1)C\theta_2+m_{Ft}\dot{\beta}^2({}^ay_{Ft}S\theta_1-{}^az_{Ft}C\theta_1)C\theta_2$$

$$+m_{Sk}L_{Sk\_com}[\dot{\theta}_2^2+C^2\theta_2(\dot{\theta}_1+\dot{\beta})^2] \quad (66)$$

Substituting (39), (58), (59), (60), (61), (62), and (63) into (51) yields $$^kM_{kx}=-{}^aM_{F/T\_x}C\theta_2C\theta_3-{}^aM_{F/T\_y}(S\theta_1S\theta_2C\theta_3+C\theta_1S\theta_3)+{}^aM_{F/T\_z}(C\theta_1S\theta_2C\theta_3-S\theta_1S\theta_3)$$

$$-{}^aF_{F/T\_x}[{}^ay_{F/T}(C\theta_1S\theta_2C\theta_3-S\theta_1S\theta_3)+{}^az_{F/T}(S\theta_1S\theta_2C\theta_3+C\theta_1S\theta_3)-L_{Sk}C\theta_2S\theta_3]$$

$$+{}^aF_{F/T\_y}[{}^ax_{F/T}(C\theta_1S\theta_2C\theta_3-S\theta_1S\theta_3)+{}^az_{F/T}C\theta_2C\theta_3+L_{Sk}(S\theta_1S\theta_2C\theta_3-C\theta_1S\theta_3)]$$

$$+{}^aF_{F/T\_z}[{}^ax_{F/T}(S\theta_1S\theta_2C\theta_3+C\theta_1S\theta_3)-{}^ay_{F/T}C\theta_2C\theta_3-L_{Sk}(C\theta_1S\theta_2C\theta_3-S\theta_1S\theta_3)]$$

$$+\{-(m_F L_{Sk}+m_{Sk}L_{Sk\_com})C\theta_2S\theta_3$$

$$+m_{Ft}[{}^ay_{Ft}(C\theta_1S\theta_2C\theta_3-S\theta_1S\theta_3)+{}^az_{Ft}(S\theta_1S\theta_2C\theta_3+C\theta_1S\theta_3)]\}{}^o\ddot{x}_a$$

$$+\langle (m_F L_{Sk}+m_{Sk}L_{Sk\_com})[-S(\beta+\theta_1)S\theta_2S\theta_3+C(\beta+\theta_1)C\theta_3]$$

$$+m_{Ft}\{{}^ax_{Ft}[-C(\beta+\theta_1)S\theta_2C\theta_3+S(\beta+\theta_1)S\theta_3]-({}^ay_{Ft}S\beta+{}^az_{Ft}C\beta)C\theta_2S\theta_3\}\rangle{}^o\ddot{y}_a$$

$$+\langle (m_{Ft}L_{Sk}+m_{Sk}L_{Sk\_com})[C(\beta+\theta_1)S\theta_2S\theta_3+S(\beta+\theta_1)C\theta_3]$$

$$-m_{Ft}\{{}^ax_{Ft}[S(\beta+\theta_1)S\theta_2C\theta_3+C(\beta+\theta_1)S\theta_3]-({}^ay_{Ft}C\beta-{}^az_{Ft}S\beta)C\theta_2S\theta_3\}\rangle({}^o\ddot{z}_a+g)$$

$$+({}^kI_{Sk\_x}+m_{Sk}L_{Sk\_com}^2)C\theta_2C\theta_3(\ddot{\theta}_1+\ddot{\beta})+({}^kI_{Sk\_x}+m_{Sk}L_{Sk\_com}^2)S\theta_3\dot{\theta}_2$$

$$+\langle [{}^aI_{Ft\_x}+m_{Ft}({}^ay_{Ft}^2+{}^az_{Ft}^2)]C\theta_2C\theta_3$$

$$+m_{Ft}\{L_{Sk}[{}^ay_{Ft}(C\theta_1S\theta_2C\theta_3+S\theta_1C\theta_3)+{}^az_{Ft}(S\theta_1S\theta_2S\theta_3-C\theta_1C\theta_3)]$$

$$-{}^ax_{Ft}[{}^ay_{Ft}(S\theta_1S\theta_2C\theta_3+Cf_1Sf_3)+{}^az_{Ft}(-C\theta_1S\theta_2C\theta_3+S\theta_1S\theta_3)]\}\rangle\ddot{\beta}$$

$$+({}^kI_{Sk\_y}-{}^kI_{Sk\_z}+m_{Sk}L_{Sk\_com}^2)C\theta_2S\theta_2C\theta_3\dot{\theta}_1^2+\langle ({}^kI_{Sk\_y}-{}^kI_{Sk\_z}+m_{Sk}L_{Sk\_com}^2)C\theta_2S\theta_2S\theta_3$$

$$+m_{Ft}\{L_{Sk}[{}^ay_{Ft}(S\theta_1S\theta_2S\theta_3-C\theta_1C\theta_3)-{}^az_{Ft}(C\theta_1S\theta_2S\theta_3+S\theta_1C\theta_3)]$$

$$+{}^ax_{Ft}[{}^ay_{Ft}(C\theta_1S\theta_2C\theta_3-S\theta_1S\theta_3)+{}^az_{Ft}(S\theta_1S\theta_2C\theta_3+C\theta_1S\theta_3)]\}\rangle\dot{\beta}^2$$

$$-({}^kI_{Sk\_x}+{}^kI_{Sk\_y}-{}^kI_{Sk\_z}+2m_{Sk}L_{Sk\_com}^2)S\theta_2C\theta_3(\dot{\theta}_1+\dot{\beta})\dot{\theta}_2$$

$$+({}^kI_{Sk\_x}-{}^kI_{Sk\_y}+{}^kI_{Sk\_z})(S\theta_2C\theta_3\dot{\theta}_2-C\theta_2S\theta_3(\dot{\theta}_1+\dot{\beta}))\dot{\theta}_3$$

$$+({}^kI_{Sk\_y}-{}^kI_{Sk\_z}+m_{Sk}L_{Sk\_com}^2)S(2\theta_2)S\theta_3\dot{\theta}_1\dot{\beta} \quad (67)$$

$$^kM_{ky}={}^aM_{F/T\_x}C\theta_2S\theta_3+{}^aM_{F/T\_y}(S\theta_1S\theta_2S\theta_3-C\theta_1C\theta_3)-{}^aM_{F/T\_z}(C\theta_1S\theta_2S\theta_3+S\theta_1C\theta_3)$$

$$+{}^aF_{F/T\_x}[{}^ay_{F/T}(C\theta_1S\theta_2S\theta_3+S\theta_1C\theta_3)+{}^az_{F/T}(S\theta_1S\theta_2S\theta_3-C\theta_1C\theta_3)+L_{Sk}C\theta_2C\theta_3]$$

$$-{}^aF_{F/T\_y}[{}^ax_{F/T}(C\theta_1S\theta_2S\theta_3+S\theta_1C\theta_3)+{}^az_{F/T}C\theta_2S\theta_3-L_{Sk}(S\theta_1S\theta_2\theta_3+C\theta_1S\theta_3)]$$

$$+{}^aF_{F/T\_z}[{}^ax_{F/T}(-S\theta_1S\theta_2S\theta_3+C\theta_1C\theta_3)+{}^ay_{F/T}C\theta_2S\theta_3-L_{Sk}(C\theta_1S\theta_2\theta_3-S\theta_1S\theta_3)]$$

$$-\{(m_{Sk}L_{Sk\_com}+m_{Ft}L_{Sk})C\theta_2C\theta_3$$

$$+m_{Ft}[{}^ay_{Ft}(C\theta_1S\theta_2S\theta_3+S\theta_1C\theta_3)-{}^az_{Ft}(-S\theta_1S\theta_2S\theta_3+C\theta_1C\theta_3)]\}{}^o\ddot{x}_a$$

$$+\langle -(L_{Sk\_com}m_{Sk}+m_{Ft}L_{Sk})[S(\beta+\theta_1)S\theta_2C\theta_3+C(\beta+\theta_1)S\theta_3]$$

$$+m_{Ft}\{{}^ax_{Ft}[C(\beta+\theta_1)S\theta_2S\theta_3+S(\beta+\theta_1)C\theta_3]+({}^ay_{Ft}S\beta+{}^az_{Ft}C\beta)C\theta_2S\theta_3\}\rangle{}^o\ddot{y}_a$$

$$-\langle (m_{Sk}L_{Sk\_com}+m_{Ft}L_{Sk})[-C(\beta+\theta_1)S\theta_2C\theta_3+S(\beta+\theta_1)S\theta_3]$$

$$+m_{Ft}\{{}^ax_{Ft}[-S(\beta+\theta_1)S\theta_2S\theta_3+C(\beta+\theta_1)C\theta_3]+({}^ay_{Ft}C\beta-{}^az_{Ft}S\beta)C\theta_2S\theta_3\}\rangle({}^o\ddot{z}_a+g)$$

$$\langle -[{}^aI_{Ft\_x}+m_{Ft}({}^ay_{Ft}^2+{}^az_{Ft}^2)]C\theta_2S\theta_3$$

$$+m_{Ft}\{L_{Sk}[{}^ay_{Ft}(C\theta_1S\theta_2C\theta_3-S\theta_1S\theta_3)+{}^az_{Ft}(S\theta_1S\theta_2C\theta_3+C\theta_1S\theta_3)]$$

$$+{}^ax_{Ft}[{}^ay_{Ft}(S\theta_1S\theta_2S\theta_3-C\theta_1C\theta_3)-{}^az_{Ft}(C\theta_1S\theta_2S\theta_3+S\theta_1C\theta_3)]\}\rangle\ddot{\beta}$$

$$+({}^kI_{Sk\_y}+m_{Sk}L_{Sk\_com})[-C\theta_2S\theta_3(\ddot{\theta}_1+\ddot{\beta})+C\theta_3\dot{\theta}_2]$$

$$+({}^kI_{Sk\_x}-{}^kI_{Sk\_z}+m_{Sk}L_{Sk\_com}^2)C\theta_2S\theta_2C\theta_3[(\dot{\theta}_1^2+\dot{\beta}^2)+2\dot{\theta}_1\dot{\beta}]$$

$$+m_{Ft}\{L_{Sk}[^ay_{Ft}(S\theta_1 S\theta_2 C\theta_3+C\theta_1 S\theta_3)+^az_{Ft} \\ (-C\theta_1 S\theta_2 C\theta_3+S\theta_1 S\theta_3)]$$

$$-^ax_{Ft}[^ay_{Ft}(C\theta_1 S\theta_2 S\theta_3+S\theta_1 C\theta_3)-^az_{Ft}(-S\theta_1 S\theta_2 S\theta_3+ \\ C\theta_1 C\theta_3)]\}\dot{\beta}^2$$

$$+(^ki_{Sk\_x}-^kI_{Sk\_z}+2m_{Sk}L_{Sk\_com}^2)S\theta_2 S\theta_3 \dot{\theta}_2(\dot{\theta}_1+\dot{\beta})$$

$$+(^kI_{Sk\_x}-^kI_{Sk\_y}-^kI_{Sk\_z})\dot{\theta}_3[S\theta_3 \dot{\theta}_2+C\theta_2 C\theta_3(\dot{\theta}_1+\dot{\beta})]$$

$$-^kI_{Sk\_y}S\theta_2 S\theta_3 \dot{\theta}_2 \dot{\beta} \qquad (68)$$

$$^kM_{kz}=-^aM_{F/T\_x}S\theta_2+(^aM_{F/T\_y}S\theta_1-^aM_{F/T\_z}C\theta_1)C\theta_2$$

$$+^aF_{F/T\_x}(^ay_{F/T}C\theta_1+^az_{F/T}S\theta_1)C\theta_2$$

$$-^aF_{F/T\_y}(^ax_{F/T}C\theta_1 C\theta_2-^az_{F/T}S\theta_2)$$

$$-^aF_{F/T\_z}(^ax_{F/T}S\theta_1 C\theta_2+^ay_{F/T}S\theta_2)$$

$$-m_{Ft}{}^o\ddot{x}_a(^ay_{Ft}C\theta_1+^az_{Ft}S\theta_1)C\theta_2$$

$$-m_{Ft}{}^o\ddot{y}_a[^ax_{Ft}C(\beta+\theta_1)C\theta_2+(^ay_{Ft}S\beta+^az_{Ft}C\beta)S\theta_2]$$

$$+m_{Ft}(^o\ddot{z}_a+g)[^ax_{Ft}S(\beta+\theta_1)C\theta_2+(^ay_{Ft}C\beta-^az_{Ft}S\beta)S\theta_2]$$

$$+^kI_{Sk\_z}[S\theta_2(\ddot{\theta}_1+\ddot{\beta})+\ddot{\theta}_3]$$

$$+\{^aI_{Ft\_x}S\theta_2+m_{Ft}[^ax_{Ft}(^ay_{Ft}S\theta_1-^az_{Ft}C\theta_1)C\theta_2+ \\ (^ay_{Ft}^2+^az_{Ft}^2)S\theta_2]\}\ddot{\beta}$$

$$+[-m_{Ft}{}^ax_{Ft}(^ay_{Ft}S\theta_1+^az_{Ft}C\theta_1)+(^kI_{Sk\_y}-^kI_{Sk\_x}) \\ C\theta_2 S\theta_3 C\theta_3]C\theta_2 \dot{\beta}^2$$

$$+C\theta_2[^kI_{Sk\_z}+(^kI_{Sk\_y}-^kI_{Sk\_x})C(2\theta_3)](\dot{\theta}_1+\dot{\beta})\dot{\theta}_2$$

$$+(^kI_{Sk\_x}-^kI_{Sk\_y})S\theta_3 C\theta_3[\dot{\theta}_1{}^2 C^2\theta_2-\dot{\theta}_2{}^2]$$

$$+2(^kI_{Sk\_x}-^kI_{Sk\_y})C^2\theta_2 S(2\theta_3)\dot{\theta}_1 \dot{\beta} \qquad (69)$$

Thus, all moments and forces at knee and ankle are obtained. With close observation of (53), (55), (56), (57), (64), (65), (66), (67), (68) and (69), it is clear that the knee and ankle moments and forces can be computed in real-time with online measurements of four angles (i.e., footplate angle ($\beta$), dorsiflexion/planar-flexion angle $\theta_1$, inversion/eversion angle $\theta_2$, shank internal/external rotation angle $\theta_3$), which can be measured with the 6-DOF goniometer in FIG. 5 and FIG. 6, and three forces and three moments acting on foot (i.e., $aF_{F/T\_x}$, $^aF_{F/T\_y}$, $^aF_{F/T\_z}$, $^aM_{F/T\_x}$, $^aM_{F/T\_y}$, $^aM_{F/T\_z}$), which can be measured with the 6-axis F/T sensor. Note that, two of the moments applied from footplate to foot ($^aM_{F/T\_x}$ and $^aM_{F/T\_y}$) are not required for calculation of moments of lower limb joints, if foot is not strapped to footplate (Winter, 2005).

Of course, mass of shank and foot ($m_{Sk}$, $m_{Ft}$), inertias of shank ($^kI_{Sk\_x}$, $^kI_{Sk\_y}$, $^kI_{Sk\_z}$) and foot ($^aI_{Ft\_x}$), and segment lengths ($L_{Sk}$, $L_{Sk\_com}$) are also required. However, these are constant values for each subject and can be measured/estimated offline. Masses and inertias can be estimated by referring anthropometric data (Winter, 2005; Zatsiorsky, 2002), and segment lengths can be either measured using a simple digitizer (e.g., MicroScribe or a digitizing probe of Optotrak) or estimated by referring anthropometry (Winter, 2005; Zatsiorsky, 2002).

Variables needed to be measured from the goniometer and force/torque sensor below the foot in real-time for calculation of each joint moment and for are listed in FIG. 7 as a summary. Clearly, one can see depends on the joint and forces/moments of interest, number of required variables vary.

3. Feasibility Testing Experiment

1) A Sample Experimental Setup

A modified ET (e.g., Reebok Spacesaver RL) was instrumented with 6-axis F/T sensors (e.g., JR3 Inc., Woodland, Calif.) on both sides underneath the footplate. The ankle joint center (JC), midpoint between the medial and lateral malleoli, was aligned with the F/T sensor center. One end of the 6-DOF goniometer was attached to the footplate and the other end was strapped to the bony frontal-medial surface of shank. To corroborate the estimated Knee Adduction Moment (KAM) using the 6-DOF goniometer, an Optotrak 3020 system with 3 sets of markers (4 markers/set attached to a rigid shell) attached on thigh, shank, and foot was also used. The F/T and goniometer data were sampled at 1 KHz and the Optotrak data at 50 Hz. The foot was strapped to the footplate with no relative motions to the footplate. As an initial calibration, the subject stood still and initial knee JC coordinates with respect to the ankle frame was determined. From anthropometry data (Winter, 2005; Zatsiorsky, 2002), lengths—between knee JC and COM of shank and between knee JC and ankle JC—and masses and inertias with respect to COM of foot and to that of shank were obtained. With all the measured/estimated kinematic and kinetic variables, KAM was computed with respect to the knee local coordinate system and displayed as external KAM following the convention in (Foroughi et al., 2009).

2) Results

The KAM during stepping movement was estimated on a healthy volunteer (male, age: 32; height: 181 cm; mass: 97 kg). Strong KAM was generated during the stepping movement and the moment varied systematically with the stepping cycle (FIG. 6 (a)). When the subject adducted the knee during stepping, the KAM increased markedly (FIG. 6(b)). Furthermore, KAM estimated using the 6-DOF goniometer matched closely with that using the Optotrak and especially the peak KAM locations in each cycle with the 6-DOF goniometer and that with Optotrak are almost identical, thereby confirming the effectiveness of the proposed method.

What is claimed is:

1. An exercise apparatus comprising:
   a 3-dimensional coordinate system having an x-axis, a y-axis, and a z-axis;
   lower limb segments;
   a moving arm;
   a multi-axis force sensor;
   at least one footplate attached to said multi-axis force sensor for supporting a human foot or shoe;
   a compact real-time ankle motion measurement device, said motion measurement device adapted to be attached between the leg and foot and capable of measuring the ankle joint motion in at least one degree of freedom;
   a central processor, said central processor capable of calculating lower-limb joint moments in real time;
   wherein the central processor calculates lower-limb joint moments with a modified inverse dynamic method, which does not involve computation of a location of center of pressure.

2. The apparatus of claim 1, wherein said modified inverse dynamics method measures ankle kinematics using said compact real-time ankle motion measurement device and measures ground reaction forces and moments by a multi-axis force sensor adapted to be attached underneath the foot, and with the footplate adapted to fix the foot of the user, ankle and knee joint forces/moments can be calculated without calculating the center of pressure.

3. The apparatus of claim 1, wherein the apparatus further comprises a real-time feedback device, said real-time feedback device capable of displaying lower-limb joint moments or generating visual or audio or haptic feedback in response to an amplitude/timing of the lower-limb joint moments.

4. The apparatus of claim 1, wherein said motion measurement device is either at least one multi-degree-of-freedom ankle goniometer or at least one multi-degree-of-freedom inertial measurement unit.

5. The apparatus of claim 4, wherein said multi-degree-of-freedom goniometer comprises a first end and a second end, said first end attached to said footplate and said second end adapted to be attached to a leg of a user, said multi-degree-of-freedom goniometer capable of measuring ankle dorsiflexion/planar-flexion angles, ankle inversion/eversion angles, and shank internal/external rotation angles in real-time.

6. The apparatus of claim 4, wherein said multi-degree-of-freedom inertial measurement units are capable of being attached to said human foot or a leg of a user, said multi-degree-of-freedom inertial measurement units further capable of measuring ankle dorsiflexion/planar-flexion angles, ankle inversion/eversion angles, and shank internal/external rotation angles in real-time.

7. The apparatus of claim 4, wherein said multi-degree-of-freedom inertial measurement units are capable of being attached to a leg and a thigh of a user, said multi-degree-of-freedom inertial measurement units further capable of measuring knee flexion/extension angles, knee abduction/adduction angles, and shank internal/external rotation angles in real-time.

8. The apparatus of claim 1, wherein said footplate further comprises a foot bootstrap capable of strapping said human foot to the footplate and preventing motion of said human foot relative to said footplate.

9. The apparatus of claim 1, further comprising a pivoting or sliding mechanism capable of inducing or applying a pivoting or sliding movement to said footplate, said pivoting movement being about an axis parallel to either said z-axis or said y-axis, said sliding movement being along said x-axis and said y-axis.

10. The apparatus of claim 1, wherein said multi-axis force sensor is capable of measuring one or more ground reaction forces along said x-axis, y-axis, or z-axis and at least one of said lower-limb joint moments about said x-axis, y-axis, or z-axis.

11. The apparatus of claim 1, further comprising a foot bootstrap, wherein said central processor is capable of measuring, in real-time, one or more ground reaction forces along said x-axis, y-axis, or z-axis and at least one of said lower-limb joint moments about said x-axis, y-axis, or z-axis when said foot bootstrap is placed around or over said human foot or shoe.

12. The apparatus of claim 1, wherein said central processor is capable of measuring in real-time one or more ground reaction forces along said x-axis, y-axis, or z-axis and at least one of said lower-limb joint moments about said x-axis, y-axis, or z-axis.

13. The apparatus of claim 1, further comprising a foot bootstrap, wherein said central processor is capable of measuring, in real-time, lower-limb kinetic variables when said foot bootstrap is used, said kinetic variables including sagittal and axial or coronal ankle forces, sagittal and axial or coronal ankle moments, sagittal and axial knee forces, and sagittal, axial, and coronal knee moments.

14. The apparatus of claim 1, wherein said at least one footplate is two footplates and wherein said apparatus can be configured as a pair of lower limb joint moment measurement devices, each one of said pair of lower limb joint moment measurement devices separately attached to one of said two footplates.

15. The apparatus of claim 9, further comprising a motor, said motor being operatively engaged with at least one of said pivoting or said sliding mechanism, said motor capable of driving said pivoting or sliding movement and exerting a predetermined force to change knee loading moments.

16. The apparatus of claim 9 further comprising a position sensor, said position sensor capable of operatively measuring an internal/external pivoting motion of said human foot.

* * * * *